(12) United States Patent
Quigley et al.

(10) Patent No.: US 12,109,234 B2
(45) Date of Patent: Oct. 8, 2024

(54) ANTI-BCMA CAR T CELL COMPOSITIONS

(71) Applicant: 2seventy bio, Inc., Cambridge, MA (US)

(72) Inventors: Travis Quigley, Cohasset, MA (US); Robert Ross, Brookline, MA (US)

(73) Assignee: 2seventy bio, Inc., Cambridge, MA (US)

(*) Notice: Subject to any disclaimer, the term of this patent is extended or adjusted under 35 U.S.C. 154(b) by 193 days.

(21) Appl. No.: 16/346,393

(22) PCT Filed: Nov. 3, 2017

(86) PCT No.: PCT/US2017/059989
§ 371 (c)(1),
(2) Date: Apr. 30, 2019

(87) PCT Pub. No.: WO2018/085690
PCT Pub. Date: May 11, 2018

(65) Prior Publication Data
US 2020/0261501 A1    Aug. 20, 2020

Related U.S. Application Data

(60) Provisional application No. 62/514,401, filed on Jun. 2, 2017, provisional application No. 62/417,840, filed on Nov. 4, 2016.

(51) Int. Cl.
| | |
|---|---|
| *A61K 35/17* | (2015.01) |
| *A61K 9/00* | (2006.01) |
| *A61P 35/00* | (2006.01) |
| *C07K 14/705* | (2006.01) |
| *C07K 14/725* | (2006.01) |
| *C07K 16/28* | (2006.01) |

(52) U.S. Cl.
CPC ............ *A61K 35/17* (2013.01); *A61K 9/0019* (2013.01); *A61P 35/00* (2018.01); *C07K 14/7051* (2013.01); *C07K 14/70517* (2013.01); *C07K 14/70578* (2013.01); *C07K 16/2878* (2013.01); *C07K 2317/622* (2013.01); *C07K 2319/03* (2013.01)

(58) Field of Classification Search
CPC .............. A61K 35/17; A61K 9/0019; A61K 2039/5156; A61K 38/1774; A61P 35/00; A61P 7/00; A61P 35/02; C07K 14/7051; C07K 14/70517; C07K 14/70578; C07K 16/2878; C07K 2317/622; C07K 2319/03; C12N 2740/10041; A01K 67/0271
See application file for complete search history.

(56) References Cited

U.S. PATENT DOCUMENTS

| | | | |
|---|---|---|---|
| 5,585,089 A | 12/1996 | Queen et al. | |
| 5,827,642 A | 10/1998 | Riddell et al. | |
| 5,858,358 A | 1/1999 | June et al. | |
| 5,883,223 A | 3/1999 | Gray | |
| 5,994,136 A | 11/1999 | Naldini et al. | |
| 6,005,079 A | 12/1999 | Casterman et al. | |
| 6,013,516 A | 1/2000 | Verma et al. | |
| 6,040,177 A | 3/2000 | Riddell et al. | |
| 6,352,694 B1 | 3/2002 | June et al. | |
| 6,534,055 B1 | 3/2003 | June et al. | |
| 6,682,907 B1 | 1/2004 | Charneau et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 7,754,482 B2 | 7/2010 | Riley et al. | |
| 7,977,095 B2 | 7/2011 | Bonyhadi et al. | |
| 9,034,324 B2 | 5/2015 | Kalled et al. | |
| 9,402,865 B2 | 8/2016 | Powell et al. | |
| 9,499,629 B2 | 11/2016 | June et al. | |
| 9,765,342 B2 | 9/2017 | Kochenderfer | |
| 10,383,929 B2 | 8/2019 | Morgan et al. | |
| 10,479,975 B2 | 11/2019 | Friedman | |
| 10,624,960 B2 | 4/2020 | Morgan et al. | |
| 10,639,358 B2 | 5/2020 | Morgan et al. | |
| 10,639,359 B2 | 5/2020 | Morgan et al. | |
| 10,646,558 B2 | 5/2020 | Morgan et al. | |
| 10,774,343 B2 | 9/2020 | Morgan et al. | |

(Continued)

FOREIGN PATENT DOCUMENTS

| | | |
|---|---|---|
| AU | 2013204923 A1 | 1/2014 |
| CN | 103442768 A | 12/2013 |

(Continued)

OTHER PUBLICATIONS

Clarke et al (Cryotherapy, 11(4):472-479, 2009).*
Rizoli (PlasmaLyte The journal of TRAUMA, Injury, Infection and Critical care 70(5), May 2011, Supplement 2011 S17-18).*
Laubach et al Expert Opin Investig Drugs 23(4):445-452,2014).*
Dimopoulos et al (Nat. Rev. Clin. Onc. 12:42-54, 2015, published online Nov. 25, 2014).*
Brundo et al (Blood, 127(26):3321-3330, 2016).*
Santomasso et al (2019 ASCO Educational Book pp. 433-444.*
Walpole et. al., BMC Public Health. 12(439):1-6 (2012) (Year: 2012).*
Almagro et al., "Humanization of antibodies," Frontiers in Bioscience, 13, Jan. 1, 2008, pp. 1619-1633.

(Continued)

*Primary Examiner* — Jessica H Roark
*Assistant Examiner* — Francesca Edgingtongiordan
(74) *Attorney, Agent, or Firm* — Ariana D. Harris; Adam J. Gastonguay; Amy E. Mandragouras

(57) ABSTRACT

The invention provides improved anti-BCMA CAR T cell compositions for adoptive T cell therapy for relapsed/refractory multiple myeloma.

22 Claims, 6 Drawing Sheets

Specification includes a Sequence Listing.

(56) References Cited

U.S. PATENT DOCUMENTS

| | | |
|---|---|---|
| 11,020,466 B2 | 6/2021 | Morgan et al. |
| 11,351,236 B2 | 6/2022 | Morgan et al. |
| 11,382,965 B2 | 7/2022 | Morgan et al. |
| 11,479,755 B2 | 10/2022 | Friedman |
| 11,560,547 B2 | 1/2023 | Friedman |
| 11,633,463 B2 | 4/2023 | Morgan et al. |
| 12,006,369 B2 | 6/2024 | Morgan et al. |
| 12,029,784 B2 | 7/2024 | Morgan et al. |
| 2002/0058019 A1 | 5/2002 | Berenson et al. |
| 2002/0115214 A1 | 8/2002 | June et al. |
| 2002/0177125 A1 | 11/2002 | Kamb et al. |
| 2003/0012783 A1 | 1/2003 | Kindsvogel |
| 2003/0095955 A1 | 5/2003 | Noessner et al. |
| 2003/0147869 A1 | 8/2003 | Riley et al. |
| 2006/0099177 A1 | 5/2006 | June et al. |
| 2006/0121005 A1 | 6/2006 | Berenson et al. |
| 2008/0058019 A1 | 3/2008 | Natarajan et al. |
| 2008/0089863 A1 | 4/2008 | Mallet et al. |
| 2008/0274091 A1 | 11/2008 | Selpushkin et al. |
| 2009/0137017 A1 | 5/2009 | Bonyhadi et al. |
| 2012/0082661 A1 | 4/2012 | Kalled et al. |
| 2012/0148552 A1 | 6/2012 | Jensen |
| 2012/0301447 A1 | 11/2012 | Jensen |
| 2013/0004471 A1 | 1/2013 | Denaro et al. |
| 2013/0280220 A1 | 10/2013 | Ahmed et al. |
| 2013/0287748 A1 | 10/2013 | June et al. |
| 2013/0288368 A1 | 10/2013 | June et al. |
| 2013/0309193 A1 | 11/2013 | Weinschenk et al. |
| 2014/0004132 A1 | 1/2014 | Brenner et al. |
| 2014/0086889 A1 | 3/2014 | Battaglia et al. |
| 2014/0087462 A1 | 3/2014 | Scheffold et al. |
| 2014/0322183 A1 | 10/2014 | Milone et al. |
| 2014/0322212 A1 | 10/2014 | Brogdon et al. |
| 2015/0024482 A1 | 1/2015 | Frigault et al. |
| 2015/0051266 A1 | 2/2015 | Kochenderfer |
| 2015/0307623 A1 | 10/2015 | Abbot et al. |
| 2016/0002601 A1 | 1/2016 | Kokundkar et al. |
| 2016/0046724 A1 | 2/2016 | Brogdon et al. |
| 2017/0049819 A1 | 2/2017 | Friedman et al. |
| 2017/0051252 A1 | 2/2017 | Morgan et al. |
| 2017/0051308 A1 | 2/2017 | Morgan et al. |
| 2017/0136063 A1 | 5/2017 | Perez et al. |
| 2017/0218337 A1 | 8/2017 | Friedman |
| 2017/0226216 A1 | 8/2017 | Morgan et al. |
| 2018/0085444 A1 | 3/2018 | Morgan et al. |
| 2018/0147271 A1 | 5/2018 | Morgan et al. |
| 2018/0214527 A1 | 8/2018 | Wang et al. |
| 2019/0194615 A1 | 6/2019 | Friedman |
| 2019/0388525 A1 | 12/2019 | Morgan et al. |
| 2019/0388526 A1 | 12/2019 | Morgan et al. |
| 2019/0388527 A1 | 12/2019 | Morgan et al. |
| 2019/0388528 A1 | 12/2019 | Morgan et al. |
| 2020/0079864 A1 | 3/2020 | Morgan et al. |
| 2020/0109365 A1 | 4/2020 | Friedman |
| 2020/0261501 A1 | 8/2020 | Quigley et al. |
| 2020/0330572 A1 | 10/2020 | Morgan et al. |
| 2021/0032658 A1 | 2/2021 | Morgan et al. |
| 2021/0038705 A1 | 2/2021 | Morgan et al. |
| 2021/0052711 A1 | 2/2021 | Morgan et al. |
| 2021/0077603 A1 | 3/2021 | Morgan et al. |
| 2021/0077604 A1 | 3/2021 | Morgan et al. |
| 2022/0195060 A1 | 6/2022 | Friedman et al. |
| 2023/0193202 A1 | 6/2023 | Friedman |

FOREIGN PATENT DOCUMENTS

| | | |
|---|---|---|
| EP | 0 324 154 A2 | 7/1989 |
| EP | 0404097 A2 | 12/1990 |
| EP | 2094837 A2 | 9/2009 |
| JP | 2012-501180 | 1/2012 |
| JP | 2013-522286 | 6/2013 |
| JP | 2017-513891 A | 6/2017 |
| JP | 2020-015767 A | 1/2020 |
| RU | 2477728 C1 | 3/2013 |
| WO | WO 1993/001161 A1 | 1/1993 |
| WO | WO 1994/004678 A1 | 3/1994 |
| WO | WO 1994/025591 A1 | 11/1994 |
| WO | WO 1995/028407 | 10/1995 |
| WO | WO 1997/032970 A1 | 9/1997 |
| WO | WO 2003/057171 A2 | 7/2003 |
| WO | WO 2004/035768 A1 | 4/2004 |
| WO | WO 2004/104185 A1 | 12/2004 |
| WO | WO 2006/010834 A1 | 2/2006 |
| WO | WO 2006/090291 A2 | 8/2006 |
| WO | WO 2007/018318 A1 | 2/2007 |
| WO | WO 2008/153742 A2 | 12/2008 |
| WO | WO-2009/058564 A2 | 5/2009 |
| WO | WO 2009/091826 A2 | 7/2009 |
| WO | WO 2010/104949 A2 | 9/2010 |
| WO | WO 2011/041093 A1 | 4/2011 |
| WO | WO 2011/057124 A1 | 5/2011 |
| WO | WO 2011/114275 A1 | 9/2011 |
| WO | WO 2012/079000 A1 | 6/2012 |
| WO | WO 2012/099973 A2 | 7/2012 |
| WO | WO 2012/129514 A1 | 9/2012 |
| WO | WO 2012/140130 A1 | 10/2012 |
| WO | WO 2012/163805 A1 | 12/2012 |
| WO | WO 2012/170911 A2 | 12/2012 |
| WO | WO 2013/070468 A1 | 5/2013 |
| WO | WO 2013/126712 A1 | 8/2013 |
| WO | WO 2013/154760 A1 | 10/2013 |
| WO | WO 2014/011996 A1 | 1/2014 |
| WO | WO 2014/031687 A1 | 2/2014 |
| WO | WO 2014/039523 A1 | 3/2014 |
| WO | WO-2014/048920 A1 | 4/2014 |
| WO | WO 2014/055442 A1 | 4/2014 |
| WO | WO 2014/055668 A1 | 4/2014 |
| WO | WO 2014/055771 A1 | 4/2014 |
| WO | WO 2014/059173 A2 | 4/2014 |
| WO | WO 2014/089335 A2 | 6/2014 |
| WO | WO 2014/099671 A1 | 6/2014 |
| WO | WO 2014/100385 A1 | 6/2014 |
| WO | WO 2014/130635 A1 | 8/2014 |
| WO | WO 2014/153270 A1 | 9/2014 |
| WO | WO-2015/120096 A2 | 8/2015 |
| WO | WO 2015/123527 A1 | 8/2015 |
| WO | WO 2015/158671 A1 | 10/2015 |
| WO | WO 2015/164739 A1 | 10/2015 |
| WO | WO 2015/164745 A1 | 10/2015 |
| WO | WO 2015/164759 A2 | 10/2015 |
| WO | WO 2015/188119 A1 | 12/2015 |
| WO | WO 2016/014789 A2 | 1/2016 |
| WO | WO 2016/094304 A2 | 6/2016 |
| WO | WO 2016/164429 A1 | 10/2016 |
| WO | WO-2017/066481 A1 | 4/2017 |
| WO | WO 2017/099712 A1 | 6/2017 |
| WO | WO 2018/085690 A1 | 5/2018 |
| WO | WO-2019/006072 A1 | 1/2019 |
| WO | WO-2019/018603 A2 | 1/2019 |
| WO | WO-2020/206061 A1 | 10/2020 |
| WO | WO-2021/109977 A1 | 6/2021 |

OTHER PUBLICATIONS

Balzano et al., "CTLA-4 and CD28: similar proteins, neighbouring genes," Int J Cancer Suppl. 1992;7:28-32.

Barthelemy et al., "Comprehensive Analysis of the Factors Contributing to the Stability and Solubility of Autonomous Human VH Domains," The Journal of Biological Chemistry, Feb. 8, 2008, vol. 283, No. 6, pp. 3639-3654.

Beiboer et al., "Guided Selection of a Pan Carcinoma Specific Antibody Reveals Similar Binding Characteristics yet Structural Divergence Between the Original Murine Antibody and its Human Equivalent," J. Mol. Biol. (2000) 296, pp. 833-849.

Choi et al., "Predicting antibody complementarity determining region structures without classification," Molecular BiosSystems, 2011, 7, pp. 3327-3334.

De Genst et al., "Antibody repertoire development in camelids," Developmental and Comparative Immunology, 30 (2006), pp. 187-198.

Edwards et al., "The Remarkable Flexibility of the Human Antibody Repertoire; Isolation of Over One Thousand Different Antibodies to a Single Protein, BLyS," J. Mol. Biol. (2003) 334, pp. 103-118.

(56) References Cited

OTHER PUBLICATIONS

Griffiths et al., "Human anti-self antibodies with high specificity from phage display libraries," The EMBO Journal, vol. 12, No. 2, 1993, pp. 725-734.

Klimka et al., "Human anti-CD30 recombinant antibodies by guided phage antibody selection using cell panning," British Journal of Cancer (2000) 83(2), pp. 252-260.

Ledbetter et al., "CD28 Ligation inT-Cell Activation: Evidence for Two Signal Transduction Pathways," Blood, vol. 75, No. 7, Apr. 1, 1990, pp. 1531-1539.

Lloyd et al., "Modelling the human immune response: performance of a 1 0 human antibody repertoire against a broad panel of therapeutically relevant antigens," Protein Engineering, Design & Selection, vol. 22, No. 3, 2009, pp. 159-168.

Park et al., "Treating Cancer with Genetically Engineered T Cells," Trends Biotechnol, Nov. 2011, 29(11), pp. 550-557.

Vidan et al., "Functional integrity of the CD28 co-stimulatory pathway in T lymphocytes from elderly subjects," Age and Ageing, 1999, 28, pp. 221-227.

Adler and Dimitrov, Therapeutic Antibodies Against Cancer, 26 Hematology/Oncology Clinics ofNorth America 447-481 (2012) ("Adler").

Ahmad et al., "scFv Antibody: Principles and Clinical Application," Clinical and Developmental Immunology, vol. 2012, Article ID 980250, 15 pages.

Atanackovic, D., et al., "CD4+CD25+FOXP3+ T Regulatory Cells Reconstitute and Accumulate In The Bone Marrow of Patients With Multiple Myeloma Following Allogeneic Stem Cell Transplantation," Haematol 93(3):423-430 (2008).

Bausch-Fluck, et al., "A Mass Spectrometric-Derived Cell Surface Protein Atlas," PLoS ONE 10(4):e0121314, pp. 1-22 (2015).

Bausch-Fluck, et al., "The in Silico Human Surfaceome," PNAS 115(46):E10988-E10997 (2018).

Beck, A., et al., "Strategies and Challenges for the Next Generation of Therapeutic Antibodies," Immunol 10:345-352 (2010).

Biagi et al., "Chimeric T-cell receptors: new challenges for targeted immunotherapy in hematologic malignancies," Haematologica 2007; 92:381-388.

Bleumer, I., et al., "A Phase II Trial of Chimeric Monoclonal Antobody G250 for Advanced Renal Cell Carcinoma Patients," Br J Cancer 90:985-990 (2004).

Braendstrup, P., et al., "The Long Road to The First FDA Approved Gene Therapy: Chimeric Antigen Receptor T Cells Targeting CD19," Cytotherapy 22(2):57-69 (2020).

Braga, W.M.T., et al., "The Role of Regulatory T Cells and TH17 Cells in Multiple Myeloma," Clin Dev Immunol 2012(293479):1-4, (2012).

Brenner, M. K. and Heslop, H.E., "Adoptive T Cell Therapy of Cancer," Curr Opin Immunol 22:251-257 (2010).

Brentjens, R.J., et al., "Genetically Targeted T Cells Eradicate Systemic Acute Lymphoblastic Leukemia Xenografts," Clin Cancer Res 13(18):5426-5435 (2007).

Brentjens, R., et al., "Treatment of Chronic Lymphocytic Leukemia With Genetically Targeted Autologous T Cells: Case Report of an unforeseen Adverse Event in a Phase I Clinical Trial," Molecular Therapy 18(4):666-668 (2010).

Brimnes, M.K. et al., "Increased Level of Both CD4+FOXP3+ Regulatory T Cells and CH14+HLA-DR-/low Myeloid-Derived Suppressor Cells and Decreased Level of Dendritic Cells in Patients with Multiple Myeloma," Clin Immunol 72:540-547 (2010).

Bross et al., "Approval Summary: Gemtuzumab Ozogamicin in Relapsed Acute Myeloid Leukemia," Clinical Cancer Research, Jun. 2001, vol. 7, 1490-1496.

Caers et al., "Multiple myeloma—an update on diagnosis and treatment," European Journal of Haematology, 2008 81 (329-343).

Cartellieri, M., et al., "Chimeric Antigen Receptor-Engineered T Cells for Immunotherapy of Cancer," J Biomed and Biotech 2010(956304):1-13 (2010).

Ch'en et al., "Characterisation of monoclonal antibodies to the TNF and TNF receptor families," Cellular Immunology 236 (2005) 78-85.

Chauhan, A.K., "Human CD4+ T-Cells: A Role for Low-Affinity Fc Receptors," Front. Immunol. (2016) 7:215, 8 pages.

Chinnasamy et al., "Gene therapy using genetically modified lymphocytes targeting VEGFR-2 inhibits the growth of vascularized syngenic tumors in mice," J Clin Invest. 2010;120(11):3953-3968.

Cho et al., "Targeting B Cell Maturation Antigen (BCMA) in Multiple Myeloma: Potential Uses of BCMA-Based Immunotherapy," Front. Immunol. (2018) 9:1821.

De Claro, "U.S. Food and Drug Administration Approval Summary: Brentuximab Vedotin for the Treatment of Relapsed Hodgkin Lymphoma or Relapsed Systemic Anaplastic Large-Cell Lymphoma," Clin Cancer Res; 2012; 18(21); 5845-9.

Demko et al., "FDA Drug Approval Summary: Alemtuzumab as Single-Agent Treatment for B- Cell Chronic Lymphocytic Leukemia," The Oncologist 2008;13:167-174.

Di Bernardo, A., et al., "Humoral Immunotherapy of Multiple Myeloma: Perspectives and Perplexities," Expert Opin. Biol. Ther. 10(6):863-873 (2010).

Di Stassi et al., "T lymphocytes coexpressing CCR4 and a chimeric antigen receptor targeting CD30 have improved homing and antitumor activity in a Hodgkin tumor model," Blood, Jun. 18, 2009, vol. 113, No. 25, 6392-6402.

Dimopoulos and Terpos, "Multiple myeloma," Annals of Oncology 21 (Supplement 7): vii143-vii150, 2010.

Eshhar et al., "Specific activation and targeting of cytotoxic lymphocytes through chimeric single chains consisting of antibody-binding domains and the γ or ζ subunits of the immunoglobulin and T-cell receptors," PNAS USA, Jan. 1993, vol. 90, pp. 720-724.

Feyler, S., et al., "CD4+CD35+FoxP3+ Regulatory T Cells are Increase Whilst CD3+CD4-CD8- αβTCR+ Double Negative T Cells are Decreased the Peripheral Blood of Patients with Multiple Myeloma Which Correlates With Disease Burden," Br J Haematol 144:686-695 (2009).

Finney et al., "Activation of resting human primary T cells with chimeric receptors: costimulationfrom CD28, inducible costimulator, CD134, and CD137 in series with signals from the TCRζ chain," J Immunol 2004; 172:104-113.

Finney et al., "Chimeric receptors providing both primary and costimulatory signaling in T cells from a single gene product," J Immunol 1998; 161:2791-2797.

Geffen and Man, "New Drugs for the Treatment of Cancer, 1990-2001," IMAJ 2002;4:1124-1131.

Gentile, M., et al., "Emerging Biological Insights and Novel Treatment Strategies in Multiple Myeloma," Expert Opin Emerg Drugs 17(3):407-438 (2012).

Giannopoulos, K., et al., "The Frequency of T Regulatory Cells Modulates the Survival of Multiple Myeloma Patients: Detailed Characterisation of Immune Status in Multiple Myeloma," Br J Cancer 106:546-552 (2012).

Gross et al., "Expression of immunoglobulin-T-cell receptor chimeric molecules as functional receptors with antibody-type specificity," PNAS USA, Dec. 1989, vol. 86, pp. 10024-10028.

Guidance for Industry, Estimating the Maximum Safe Starting Dose in Initial Clinical Trials for Therapeutics in Adult Healthy Volunteers, U.S. Department of Health and Human Services Food and Drug Administration, Center for Drug Evaluation and Research (CDER), Jul. 2005, 32 pages.

Gupta et al., "Flow Cytometric Immunophenotyping and Minimal Residual Disease Analysis in Multiple Myeloma," Am J Clin Pathol 2009;132:728-732.

Hajela, K., "Structure and Function of Fc Receptors," Biochemical Education 19(2):50-57 (1991).

Hammer, O., "CD19 as an attractive target for antibody-based therapy," mAbs; Sep./Oct. 2012, 4:5, 571-577.

Haynes et al., "Single-chain antigen recognition receptors that costimulate potent rejection of established experimental tumors," Blood, 2002; 100(9): 3155-3163.

(56) References Cited

OTHER PUBLICATIONS

Hombach et al., "An Anti-CD30 Chimeric Receptor That Mediates CD3-ζ-independent T-Cell Activation against Hodgkin's Lymphoma Cells in the Presence of Soluble CD301," Cancer Research, Mar. 15, 1998, 58, 1116-1119.

Huang et al., "Recent advances in CAR-T cell engineering," Journal of Hematology & Oncology (2020) 13:86, 19 pages.

Huston et al., "Protein engineering of antibody binding sites: recovery of specific activity in an anti-digoxin single-chain Fv analogue produced in *Escherichia coli*," PNAS USA, Aug. 1988, vol. 85, pp. 5879-5883.

Imai et al., "Chimeric receptors with 4-1BB signaling capacity provoke potent cytotoxicity against acute lymphoblastic leukemia," Leukemia (2004) 18, 676-684.

Imai, C., et al., "Genetic Modification of Primary Natural Killer Cells Overcomes Inhibitory Signals and Induces Specific Killing of Leukemic Cells," Blood 106(1):376-383 (2005).

James and Kipp, "Rituximab in Chronic Lymphocytic Leukemia," Adv Ther (2011) 28(7):534-554.

Jena et al., "Redirecting T-cell specificity by introducing a tumor-specific chimeric antigen receptor," Blood, 2010; 116(7):1035-1044.

Jensen et al., "Antitransgene Rejection Responses Contribute to Attenuated Persistence of Adoptively Transferred CD20/CD19-Specific Chimeric Antigen Receptor Redirected T Cells in Humans," Biol Blood Marrow Transplant 16: 1245-1256 (2010).

Kalos et al., "T Cells with Chimeric Antigen Receptors Have Potent Antitumor Effects and Can Establish Memory in Patients with Advanced Leukemia," Science Translational Medicine, Aug. 2011, vol. 3., Issue 95, 95ra73, 13 pages.

Kochenderfer, J.N., et al., "A Phase I Clinical Trial of Treatment of B-Cell Malignancies with Autologous Anti-CD19-CAR-Transduced T Cells," Blood (2010) 116 (21): 2865.

Kochenderfer, J.N., et al., "B-cell depletion and remissions of malignancy along with cytokine-associated toxicity in a clinical trial of anti-CD19 chimeric-antigen-receptor-transduced T cells," Blood, 2012; 119(12): 2709-2720.

Kochenderfer, J.N., et al., "Chimeric Antigen Receptor-Modified T Cells in CLL," N Engl J Med 365;20: 1937-1939 (published: 2011).

Kochenderfer, J.N., et al., "Eradication of B-lineage cells and regression of lymphoma in a patient treated with autologous T cells genetically engineered to recognize CD19," Blood, 2010;116(20): 4099-4102.

Kumar et al., "Improved survival in multiple myeloma and the impact of novel therapies," Blood, 2008;111:2516-2520.

Lamers, C.H.J., et al., "Treatment of Metastatic Renal Cell Carcinoma With Autologous T-Lymphocytes Genetically Retargeted Against Carbonic Anhydrase IX: First Clinical Experience," J Clin Oncol 24(13):e20-e22 (2006).

Lantis et al., "Redirected Antitumor Activity of Primary Human Lymphocytes Transduced With a Fully Human Anti-mesothelin Chimeric Receptor," Molecular Therapy, Mar. 2012, vol. 20, No. 3, 633-643.

Lin et al., "Flow Cytometric Immunophenotypic Analysis of 306 Cases of Multiple Myeloma," Am J Clin Pathol 2004;121:482-488.

Lo et al., "Anti-GD3 Chimeric sFv-CD28/T-Cell Receptor ζ Designer T Cells for Treatment of Metastatic Melanoma and Other Neuroectodermal Tumors," Clin Cancer Res; 16(10); May 11, 2010, pp. 2769-2780.

Mahindra, A., et al., "Latest Advances And Current Challenges In The Treatment of Multiple Myeloma," Nat. Rev. Clin. Oncol. 9:135-143 (2012).

Mitsiades, C.S., et al., "Future Directions of Next-Generation Novel Therapies, Combination Approaches, and the Development of Personalized Medicine in Myeloma," J Clin Oncol 29(14):1916-1923 (2011).

Morgan, G., "Future Drug Developments in Multiple Myeloma: An Overview of Novel Lenalidomide-Based Combination Therapies," Blood Reviews 24(1):S27-S32 (2010).

Morgan, R., et al., "Case report of a Serious Adverse Event Following the Administration of T Cells Transduced With a Chimeric Antigen Receptor Recognizing ERBB2," Mol Therapy 18(4):843-851 (2010).

Nicholson et al., "Construction and characterisation of a functional CD19 specific single chainFv fragment for immunotherapy of B lineage leukaemia and lymphoma," Molecular Immunology, 1997, vol. 34, No. 16-17, pp. 1157-1165.

Palumbo and Anderson, "Multiple Myeloma," The New England Journal of Medicine, 2011;364:1046-60.

Park, J.H. and Brentjens, R.J., "Adoptive Immunotherapy for Bcell Malignancies With Autologous Chimeric Antigen Receptor Modified Tumor Targeted T Cells," Discov Med. 9(47):277-288 (2010).

Payandeh et al., "The applications of anti-CD20 antibodies to treat various B cells disorders," Biomedicine & Pharmacotherapy 109 (2019) 2415-2426.

Pegram, H.J., et al., "Tumor-Targeted T Cells Modified to Secrete IL-12 Eradicate Systemic Tumors Without Need For Prior Conditioning," Blood 119(18):4133-4141 (2012).

Pizzolo and Roamgnani et al., "CD30 molecule (Ki-1 Ag): more than just a marker of CD30+ lymphoma," Haematologica 1995; 80:357-366.

Polonelli, L., et al., "Antibody Complementarity-Determining Regions (CDRs) Can Display Differential Antimicrobial, Antiviral and Antitumor Activities," PLsS One 3(6):e2371, pp. 1-9 (2008).

Porter et al., "Chimeric Antigen Receptor-Modified T Cells in Chronic Lymphoid Leukemia," N Engl J Med 2011;365:725-33.

Preithner et al., "High concentrations of therapeutic IgG1 antibodies are needed to compensate for inhibition of antibody-dependent cellular cytotoxicity by excess endogenous immunoglobulin G," Mol Immunol., (2006) 43:1183-1193.

Prescribing label for KYMRIAH® (tisagenlecleucel), 24 pages (2017).

Raab et al., "Multiple myeloma," Lancet 2009; 374: 324-39.

Rajkumar, S.V., "Multiple Myeloma," Curr Probl Cancer 2009;33:7-64.

Ramos and Dotti, "Chimeric antigen receptor (CAR)-engineered lymphocytes for cancer therapy," Expert Opinion on Biological Therapy, (2011) 11:7, 855-873.

Rosenberg et al., "Personalized Cell Transfer Immunotherapy for B-Cell Malignancies and Solid Cancers," Molecular Therapy, Nov. 2011, vol. 19, No. 11, 1928-1930.

Sadelain, M., et al., "The Promise and Potential Pitfalls of Chimeric Antigen Receptors," Curr Opin Immunol. 21:215-223 (2009).

Saini, K., et al., "Beyond Trastuzumab: New Treatment Options for HER2-Positive Breast Cancer," The Breast 20:S20-S27, (2011).

Savoldo et al., "CD28 costimulation improves expansion and persistence of chimeric antigen receptor-modified T cells in lymphoma patients," J Clin Invest. 2011;121(5):1822-1826.

Scott, A.M., et al., "Antibody Therapy of Cancer," Nat Rev Cancer 12:278-287 (2012).

Shirasu et al., "Construction and Molecular Characterization of Human Chimeric T-Cell Antigen Receptors Specific for Carcinoembryonic Antigen," Anticancer Research (2010) 33: 2731-2738.

Thistlethwaite et al., "Engineering T-cells with antibody-based chimeric receptors for effective cancer therapy," Current Opinion in Molecular Therapeutics 2005 7(1):48-55.

Till et al., "CD20-specific adoptive immunotherapy for lymphoma using a chimeric antigen receptor with both CD28 and 4-1BB domains: pilot clinical trial results," Blood, 2012; 119(17):3940-3950.

van de Donk, N.W.C.J., et al., "Monoclonal antibody-based therapy as a new treatment strategy in multiple myeloma," Leukemia 26:199-213 (2012).

Westwood et al., "Adoptive transfer of T cells modified with a humanized chimeric receptor gene inhibits growth of Lewis-Y-expressing tumors in mice," PNAS, Dec. 27, 2005, vol. 102, No. 52, pp. 19051-19056.

Zhang et al., "Engineering CAR-T cells," Biomarker Research (2017) 5:22, 6 pages.

(56) References Cited

OTHER PUBLICATIONS

Zhao et al., "A herceptin-based chimeric antigen receptor with modified signaling domains leads to enhanced survival of transduced T lymphocytes and antitumor activity," J Immunol 2009; 183:5563-5574.
Kalled Sequence Listing from WO 2010/104949 A2 (Sep. 16, 2010) ("Kalled Sequence Listing").
Allan et al., "Generation of Potent and Stable Human CD4+ T Regulatory Cells by Activation-independent Expression of FOXP3," www.moleculartherapy.org vol. 16 No. 1, 194-202 Jan. 2008.
Anonymous: "Study of bb2121 in Multiple Myeloma—Tabular View—ClinicalTrials.gov", (Jan. 20, 2016), XP055697969, Retrieved from the Internet: URL:https://clinicaltrials.gov/ct2/show/record/NCT02658929.
Astrakhan et al., "Ubiquitous high-level gene expression in hematopoietic lineages provides effective lentiviral gene therapy of murine Wiskott-Aldrich syndrome," Blood. May 10, 2012; 119(19): 4395-4407.
Aviles Mendoza et al., "Comparison of Five Retrovirus Vectors Containing the Human IL-2 Receptor g Chain Gene for Their Ability to Restore T and B Lymphocytes in the X-Linked Severe Combined Immunodeficiency Mouse Model," Molecular Therapy vol. 3, No. 4, Apr. 2001, 9 pages.
Berdeja et al., "Durable Clinical Responses in Heavily Pretreated Patients withRelapsed/Refractory Multiple Myeloma: Updated Results from a Multicenter Study of bb2121 Anti-Bcma CAR T Cell Therapy," Blood, American Society of Hematology, Dec. 7, 2017, 7 pages.
Dienstmann et al., "Picking the Point of Inhibition: A Comparative Review of PI3K/AKT/mTOR Pathway Inhibitors," Molecular Cancer Therapeutics, 13(5):1021-1031, Apr. 18, 2014.
European Application No. EP 15782739.5, Notice of Opposition dated Oct. 2, 2020, 9 pages.
European Application No. EP 19193858.8, Extended European Search Report dated Feb. 21, 2020, 10 pages.
European Application No. EP 19210785.2, Extended European Search Report dated Feb. 21, 2020, 9 pages.
European Application No. EP 17867273.9, Extended European Search Report dated Jun. 3, 2020, 9 pages.
European Application No. EP 20170239.6, Extended European Search Report dated Sep. 18, 2020, 11 pages.
Fedorov VD et al., "PD-1- and CTLA-4-Based Inhibitory Chimeric Antigen Receptors (iCARs) Divert Off-Target Immunotherapy Responses", Sci Transl Med, 2013, vol. 5, No. 215, pp. 1-25.
Han et al., "Chimeric antigen receptor-engineered T cells for cancer immunotherapy: progress and challenges," Journal of Hematology & Oncology, Jul. 8, 2013, 6:47, 7 pages.
Oh et al., "Lentiviral vector design using alternative RNA export elements," Retrovirology, 2007, 4:38, 10 pages.
Sadelain M et al., "The basic principles of chimeric antigen receptor (CAR) design", Cancer Discov, 2013, vol. 3, No. 4, pp. 388-398.
Sigma-Aldrich, "Cryopreservation", BIOFILES, vol. 5, No. 4, pp. 1-22, published 2010.
Steiner Normann et al: "CAR-T cells in multiple myeloma: current status", Magazine of European Medical Oncology, vol. 13, No. 1, (Jan. 16, 2020), pp. 43-49, XP037049818.
Zhong, X. et al., "Chimeric antigen receptors combining 4-1BB and CD28 signaling domains augment PI3kinase/AKT/Bcl-XL activation and CD8+ T cell-mediated tumor eradication", Mol Ther (2010);18(2):413-20.
"Proleukin for Injection (Chiron)" 2000. 14 pages, downloaded from https://theodora.com/drugs/proleukin_for_injection_chiron.html on Apr. 28, 2018.
Ali, et al., "T cells expressing an anti-B-cell maturation antigen chimeric antigen receptor cause remissions of multiple myeloma." Blood (2016); 128 (13): 1688-1700. Prepublished online Jul. 13, 2016.
Alt and Caselmann. "Liver-directed gene therapy: molecular tools and current preclinical and clinical studies", Journal of Hepatology (1995); 23: 746-758.
Asheuer, M. et al., "Human CD34+ Cells Differentiate into Microglia and Express Recombinant Therapeutic Protein", Proceedings of the National Academy of Sciences USA (2004); 101.10: 3557-3562.
Ashwood-Smith, "Preservation of Mouse Bone Marrow at -79° C. with Dimethyl Sulphoxide." Nature (1961); 190: 1204-1205.
Avery, Danielle T., et al. "BAFF selectively enhances the survival of plasmablasts generated from human memory B cells." The Journal of Clinical Investigation (2003); 112.2: 286-297.
Battaglia et al., "Rapamycin selectively expands CD4+CD25+ FoxP3+ regulatory T cells", Blood (2005); 105(12): 4743-4748.
Bellucci, Roberto, et al. "Graft-versus-tumor response in patients with multiple myeloma is associated with antibody response to BCMA, a plasma-cell membrane receptor." Blood (2005); 105.10: 3945-3950.
Bird, Robert E., et al. "Single-chain antigen-binding proteins." Science (1988); 242.4877: 423-427.
Borden and Kabat, "Nucleotide sequence of the cDNAs encoding the variable region heavy and light chains of a myeloma protein specific for the terminal nonreducing end of alpha (1----6) dextran", Proc Natl Acad Sci U S A (1987); 84 (8):2440-2443.
Brody and Crystal, "Adenovirus-mediated in vivo gene transfer", Ann. N. Y. Acad. Sci. (1994); 716: 90-101; discussion 101-3.
Carell, Thomas, et al. "A novel procedure for the synthesis of libraries containing small organic molecules." Angewandte Chemie International Edition in English (1994); 33.20: 2059-2061.
Carell, Thomas, et al. "A Solution-Phase Screening Procedure for the Isolation of Active Compounds from a Library of Molecules." Angewandte Chemie International Edition in English (1994); 33.20: 2061-2064.
Carpenito, Carmine, et al. "Control of large, established tumor xenografts with genetically retargeted human T cells containing CD28 and CD137 domains." Proceedings of the National Academy of Sciences USA (2009); 106.9: 3360-3365.
Carpenter, Robert O., et al. "B-cell maturation antigen is a promising target for adoptive T-cell therapy of multiple myeloma." Clinical Cancer Research (2013); 19.8: 2048-2060.
Challita, P. et al., "Multiple modifications in cis elements of the long terminal repeat of retroviral vectors lead to increased expression and decreased DNA methylation in embryonic carcinoma cells." J Virol. (1995); 69(2): 748-755.
Chan, W.K., et al. "Chimeric antigen receptor-redirected CD45RA-negative T cells have potent antileukemia and pathogen memory response without graft-versus-host activity." Leukemia (2015); 29(2): 387-395 (2015).
Chaudhary, Vijay K., et al. "A rapid method of cloning functional variable-region antibody genes in Escherichia coli as single-chain immunotoxins." Proceedings of the National Academy of Sciences (1990); 87.3: 1066-1070 (and correction).
Chiu, April, et al. "Hodgkin lymphoma cells express TACI and BCMA receptors and generate survival and proliferation signals in response to BAFF and APRIL." Blood (2007); 109.2: 729-739.
Cho, Charles Y., et al. "An unnatural biopolymer." Science (1993); 261: 1303-1304.
Chothia and Lesk, "Canonical structures for the hypervariable regions of immunoglobulins", J Mol Biol (1987); 196(4):901-917.
Chothia, C. et al., "Conformations of immunoglobulin hypervariable regions", Nature (1989); 342(6252):877-883.
Clever, J. et al., "RNA Secondary Structure and Binding Sites for gag Gene Products in the 5' Packaging Signal of Human Immunodeficiency Virus Type 1." J. of Virology (1995); 69(4): 2101-2109.
Cooper, Laurence JN, et al. "T-cell clones can be rendered specific for CD19: Toward the selective augmentation of the graft-versus-B-lineage leukemia effect." Blood (2003); 101.4: 1637-1644.
Cribbs, A.P., et al., "Simplified production and concentration of lentiviral vectors to achieve high transduction in primary human T cells." BMC Biotechnology (2013); 13(1): 98.
Cullen and Greene, "Regulatory Pathways Governing HIV-1 Replication", Cell (1989); 58: 423-426.
Cullen, B.R., "Human Immunodeficiency Virus as a Prototypic Complex Retrovirus", Journal of Virology (1991); 65(3): 1053-1056.

(56) References Cited

OTHER PUBLICATIONS

De Felipe, Pablo, and Ryan, Martin D. "Targeting of proteins derived from self-processing polyproteins containing multiple signal sequences." Traffic (2004); 5.8: 616-626.
De Oliveira, S.N., et al. "Modification of Hematopoietic Stem/Progenitor Cells with CD19-Specific Chimeric Antigen Receptors as a Novel Approach for Cancer Immunotherapy." Human Gene Therapy (2013); 24(10): 824-839.
De-Gang, S., et al., "In Vivo Persistence, Tumor Localization, and Antitumor Activity of CAR-Engineered T Cells Is Enhanced by Costimulatory Signaling through CD137 (4-1BB)." Cancer Research (2011), 71(13): 4617-4627.
Desjarlais, John R., and Berg, Jeremy M. "Length-encoded multiplex binding site determination: application to zinc finger proteins." Proceedings of the National Academy of Sciences (1994); 91.23: 11099-11103.
Desjarlais, John R., and Berg, Jeremy M. "Use of a zinc-finger consensus sequence framework and specificity rules to design specific DNA binding proteins." Proceedings of the National Academy of Sciences (1993); 90.6: 2256-2260.
DeWitt, S. Hobbs, et al. "'Diversomers': An approach to nonpeptide, nonoligomeric chemical diversity." Proceedings of the National Academy of Sciences USA (1993); 90.15: 6909-6913.
Donnelly, M et al., "The 'cleavage' activities of foot-and-mouth disease virus 2A site-directed mutants and naturally occurring '2A-like' sequences." J Gen Virol. (2001); 82 (Pt 5): 1027-1041.
Dull et al., "A third-generation lentivirus vector with a conditional packaging system", Journal of Virology (1998); 72(11): 8463-8671.
Esser, et al., "NK cells engineered to express a GD2-specific antigen receptor display built-in ADCC-like activity against tumor cells of neuroectodermal origin." Journal of Cellular and Molecular Medicine (2012); 16(3): 569-581.
European Application No. EP 15782739.5, Extended European Search Report dated Nov. 9, 2017, 11 pages.
European Application No. EP 15783117.3, Extended European Search Report dated Aug. 22, 2017, 8 pages.
European Application No. EP 15783862.4, Extended European Search Report dated Sep. 22, 2017, 7 pages.
European Application No. EP 15802488.5, Extended European Search Report dated Dec. 19, 2017, 11 pages.
European Application No. EP 15802488.5, Third Party Observation dated Oct. 17, 2017, 3 pages.
European Application No. EP 15824299.0, Extended European Search Report dated Dec. 13, 2017, 11 pages.
European Application No. EP 15868392.0, Extended European Search Report dated Jun. 25, 2018, 5 pages.
Ferry and Heard, "Liver-directed gene transfer vectors", Hum Gene Ther. (1998); 9(14): 1975-1981.
Friedman et al., "Effective Targeting of Multiple B-Cell Maturation Antigen-Expressing Hematological Malignances by Anti-B-Cell Maturation Antigen Chimeric Antigen Receptor T Cells," Human Gene Therapy, vol. 29, No. 5, 585-601.
Gallop, Mark A., et al. "Applications of combinatorial technologies to drug discovery. 1. Background and peptide combinatorial libraries." Journal of Medicinal Chemistry (1994); 37.9: 1233-1251.
Garfall, A.L., "Immunotherapy with Chimeric Antigen Receptors for Multiple Myeloma." Discovery Medicine: Discovery Class of Medicine, Research Technology, and T. Solariz, Inc., (2014); 17(91): 37-46.
Garland, R. J., et al. "The use of Teflon cell culture bags to expand functionally active CD8+ cytotoxic T lymphocytes." Journal of Immunological Methods (1999); 227.1: 53-63.
Gattinoni, L., et al., "Adoptive immunotherapy for cancer: building on success." Nat Rev Immunol (2006); 6(5): 383-393, 25 pages.
GenBank Accession Reference # L09137.2, "Cloning vector pUC19c", Apr. 27, 1993, 3 pages.
Giannoni, F., et al., "Allelic Exclusion and Peripheral Reconstitution by TCR Transgenic T Cells Arising From Transduced Human Hematopoietic Stem/Progenitor Cells." Molecular Therapy (2013); 21(5): 1044-1054.
Guertin, David A., and Sabatini, David M. "Defining the role of mTOR in cancer." Cancer Cell (2007); 12.1: 9-22.
Haanen, John B.A.G., et al. "Selective expansion of cross-reactive CD8+ memory T cells by viral variants." Journal of Experimental Medicine (1999); 190.9: 1319-1328.
Halene, et al., "Improved Expression in Hematopoietic and Lymphoid Cells in Mice After Transplantation of Bone Marrow Transduced With a Modified Retroviral Vector." Blood (1999); 94(10): 3349-3357.
Hirai, et al., "MK-2206, an Allosteric Aid Inhibitor, Enhances Antitumor Efficacy by Standard Chemotherapeutic Agents or Molecular Targeted Drugs In vitro and In vivo." Molecular Cancer Therapeutics (2010); 9(7): 1956-1967.
Holliger, Philipp, et al. "Diabodies": small bivalent and bispecific antibody fragments. Proceedings of the National Academy of Sciences (1993); 90.14: 6444-6448.
Holt, L. et al., "Domain antibodies: proteins for therapy", Trends in Biotechnology (2003); 21(11): 484-490.
Huang and Yen, "Role of the hepatitis B virus posttranscriptional regulatory element in export of intronless transcripts", Molecular and Cellular Biology (1995); 15(7): 3864-3869.
Hudson, Peter J., and Souriau, Christelle. "Engineered antibodies." Nature medicine 9.1 (2003): 129-134.
Huye L.E. et al. "Combining mTor inhibitors with rapamycin-resistant T cells: a two-pronged approach to tumor elimination". Molecular Therapy, 2011, 19(12): 2239-2248.
Imren, S et al., "High-level beta-globin expression and preferred intragenic integration after lentiviral transduction of human cord blood stem cells", J Clin Invest (2004); 114(7): 953-962.
International Application No. PCT/US2015/041722, International Preliminary Report on Patentability dated Jan. 24, 2017, 7 pages.
International Preliminary Report on Patentability for International Application No. PCT/US2015/027510, dated Oct. 25, 2016, 6 pages.
International Preliminary Report on Patentability for International Application No. PCT/US2015/027518, dated Oct. 25, 2016, 6 pages.
International Preliminary Report on Patentability for International Application No. PCT/US2015/027539, dated Oct. 25, 2016, 6 pages.
International Preliminary Report on Patentability for International Application No. PCT/US2015/034515, dated Dec. 5, 2016, 10 pages.
International Preliminary Report on Patentability for International Application No. PCT/US2015/064269, dated Jun. 22, 2017, 6 pages.
International Search Report and Written Opinion for International Application No. PCT/US2015/027510, dated Jul. 30, 2015, 10 pages.
International Search Report and Written Opinion for International Application No. PCT/US2015/027518, dated Jul. 30, 2015, 9 pages.
International Search Report and Written Opinion for International Application No. PCT/US2015/027539, dated Nov. 2, 2015, 6 pages.
International Search Report and Written Opinion for International Application No. PCT/US2015/034515, dated Sep. 14, 2015, 12 pages.
International Search Report and Written Opinion for International Application No. PCT/US2015/041722, dated Jan. 6, 2016, 11 pages.
International Search Report and Written Opinion for International Application No. PCT/US2015/064269, dated Feb. 23, 2016, 9 pages.
International Preliminary Report on Patentability for International Application No. PCT/US2015/064270, dated Jun. 12, 2018, 12 pages.
International Search Report and Written Opinion for International Application No. PCT/US2015/064270, dated Feb. 11, 2016, 11 pages.
International Search Report and Written Opinion for International Application No. PCT/US2017/059989, dated Feb. 5, 2018, 9 pages.
Irion, Stefan, et al. "Identification and targeting of the ROSA26 locus in human embryonic stem cells." Nature Biotechnology (2007); 25.12: 1477-1482.

(56) References Cited

OTHER PUBLICATIONS

Kalled, Susan L. "The role of BAFF in immune function and implications for autoimmunity." Immunological Reviews (2005); 204.1: 43-54.

Kay, M. A., "Adenoviral Vectors for Hepatic Gene Transfer in Animals." Chest (1997); 111: 138S-142S.

Kim, et al., "Role of PI3K/Akt signaling in memory CD8 T cell differentiation." Frontiers in Immunology (2013); 4: 20, 11 pages.

Kim, Yang-Gyun et al. "Hybrid restriction enzymes: zinc finger fusions to Fok I cleavage domain." Proceedings of the National Academy of Sciences (1996); 93.3: 1156-1160.

Kochenderfer, J.N., et al. "Adoptive Transfer of Syngeneic T Cells Transduced With a Chimeric Antigen Receptor That Recognizes Murine CD19 Can Eradicate Lymphoma and Normal B Cells." Blood (2010); 16(19): 3875-3886; Gen Bank Accession No. HM754222.1, 25 pages.

Koch-Nolte, F., "Single domain antibodies from llama effectively and specifically block T cell ecto-ADP-ribosyltransferase ART2.2 in vivo", FASEB J (2007); 21(13):3490-3498.

Koldej, R.M., et al., "Comparison of Insulators and Promoters for Expression of the Wiskott-Aldrich Syndrome Protein Using Lentiviral Vectors" Human Gene Therapy Clinical Development (2013); 24: 77-85.

Kozak, M., "An analysis of 5'-noncoding sequences from 699 vertebrate messenger RNAs", Nucleic Acids Res. (1987); 15(20): 8125-8148.

Kozak, M., "Point mutations define a sequence flanking the AUG initiator codon that modulates translation by eukaryotic ribosomes", Cell (1986); 44(2): 283-292.

Kulemzin et al., "Engineering Chimeric Antigen Receptors," Acta Naturae, vol. 9, No. 1 (32) 2017, 6-14.

Kutner et al., "Production, concentration and titration of pseudotyped HIV-1-based lentiviral vectors", Nature Protocols (2009); 4: 495-505.

Laabi, Y., et al. "A new gene, BCM, on chromosome 16 is fused to the interleukin 2 gene by at (4; 16)(q26; p13) translocation in a malignant T cell lymphoma." The EMBO Journal (1992); 11.11: 3897-3904.

Laabi, Yacine, et al. "The BCMA gene, preferentially expressed during B lymphoid maturation, is bidirectionally transcribed." Nucleic Acids Research (1994); 22.7: 1147-1154.

Landau and Littman. "Packaging system for rapid production of murine leukemia virus vectors with variable tropism." Journal of Virology (1992); 66.8: 5110-5113.

Lanitis, et al., "Chimeric Antigen Receptor T Cells with Dissociated Signaling Domains Exhibit Focused Antitumor Activity with Reduced Potential for Toxicity In Vivo." Cancer Immunology Research (2013); 1(1): 43-53, published on line Apr. 7, 2013.

Larson, S.M., et al. "Anti-CD19 chimeric antigen receptor controlled by the suicide gene HSVsr39TK in hematopoietic stem cells for immunotherapy of B-lineage malignancies." Blood (2013); 122(21): 1659.

Lee, H. C. et al. "Remission in models of type 1 diabetes by gene therapy using a single-chain insulin analogue", Nature (2000); 408(6811): 483-488.

Levitt, "Definition of an efficient synthetic poly (A) site", Genes & Development (1989); 3: 1019-1025.

Li, et al., "Optimal promoter usage for lentiviral vector-mediated transduction of cultured central nervous system cells." Journal of Neuroscience Methods (2010); 189 (1): 56-64.

Li, Qun, "Recent progress in the discovery of Akt inhibitors as anticancer agents." Expert Opinion on Therapeutic Patents (2007); 17(9): 1077-1130.

Liu and Mertz, "HnRNP L binds a cis-acting RNA sequence element that enables intron-dependent gene expression." Genes & Dev. (1995); 9: 1766-1780.

Liu, Lin, et al. "Adoptive T-cell therapy of B-cell malignancies: Conventional and physiological chimeric antigen receptors." Cancer Letters (2012); 316(1): 1-5.

Liu, Pixu, et al. "Targeting the phosphoinositide 3-kinase pathway in cancer." Nature Reviews Drug Discovery (2009); 8.8: 627-644.

Liu, Qiang, et al. "Design of polydactyl zinc-finger proteins for unique addressing within complex genomes." Proceedings of the National Academy of Sciences (1997); 94.11: 5525-5530.

Lovelock and Bishop, "Prevention of freezing damage to living cells by dimethyl sulphoxide", Nature (1959); 183(4672): 1394-1395.

Mackay, Fabienne, et al. "Baff and April: a tutorial on B cell survival." Annual Review of Immunology (2003); 21.1: 231-264.

Maier, Dawn, et al., "Development of a Simple and Robust Closed System Manufacturing Platform for T Cells Engineered With Chimeric Antigen Receptor (CAR) for Adoptive Immunotherapy." Molecular Therapy (2014); Supplement 1(22): S284.

Maldarelli et al., "Identification of posttranscriptionally active inhibitory sequences in human immunodeficiency virus type 1 RNA: novel level of gene regulation", Journal of Virology (1991); 65(11): 5732-5743.

Malim et al., "Immunodeficiency virus rev trans-activator modulates the expression of the viral regulatory genes", Nature (1988); 335: 181-183.

Meuer, Stefan C., et al. "An alternative pathway of T-cell activation: a functional role for the 50 kd T11 sheep erythrocyte receptor protein." Cell (1984); 36.4: 897-906.

Miller, A.D., "Human gene therapy comes of age." Nature (1992); 357: 455-460.

Milone, M. et al., "Chimeric receptors containing CD137 signal transduction domains mediate enhanced survival of T cells and increased antileukemic efficacy in vivo", Molecular Therapy (2009); 17(8):1453-1464.

Moreaux, Jérôme, et al. "BAFF and APRIL protect myeloma cells from apoptosis induced by interleukin 6 deprivation and dexamethasone." Blood (2004); 103.8: 3148-3157.

Movassagh, et al., "Retrovirus-Mediated Gene Transfer into T cells: 95% transduction efficiency without Further in Vitro Selection." Human Gene Therapy (2000); 11: 1189-1200.

Muyldermans, et al., "Nanobodies: Natural Single-Domain Antibodies," Annual Review of Biochemistry vol. 82:775-797 (Volume publication date Jun. 2013) First published online as a Review in Advance on Mar. 13, 2013 https://doi.org/10.1146/annurev-biochem-063011-092449.

Naldini L. et al., "Efficient transfer, integration, and sustained long-term expression of the transgene in adult rat brains injected with a lentiviral vector", Proc Natl Acad Sci USA (1996); 93(21): 11382-11388.

Naldini, L. et al., "In vivo gene delivery and stable transduction of nondividing cells by a lentiviral vector", Science (1996); 272(5259): 263-267.

Naldini, L., "Lentiviruses as gene transfer agents for delivery to non-dividing cells", Curr Opin Biotechnol. (1998); 5: 457-463.

Neri, Paola, et al. "Neutralizing B-Cell—Activating Factor Antibody Improves Survival and Inhibits Osteoclastogenesis in a Severe Combined Immunodeficient Human Multiple Myeloma Model." Clinical Cancer Research (2007); 13.19: 5903-5909.

Ng et al., "B Cell-Activating Factor Belonging to the TNF Family (BAFF)-R Is the Principal BAFF Receptor Facilitating BAFF Costimulation of Circulating T and B Cells." Journal of Immunology (2004); 173(2): 807-817.

Novak, Anne J., et al. "Expression of BCMA, TACI, and BAFF-R in multiple myeloma: a mechanism for growth and survival." Blood (2004); 103.2: 689-694.

Kochenderfer, J.N., et al., "Construction and Pre-clinical Evaluation of an Anti-CD19 Chimeric Antigen Receptor." J Immunother. (2009); 32 (7): 689-702.

O'Connor, Brian P., et al. "BCMA is essential for the survival of long-lived bone marrow plasma cells." Journal of Experimental Medicine (2004); 199.1: 91-98.

Oka, K. et al., "Recent advances in liver-directed gene therapy: implications for the treatment of dyslipidemia", Curr Opin Lipidol. (2000); 11(2): 179-186.

Orlandi, R. et al., "Cloning immunoglobulin variable domains for expression by the polymerase chain reaction", Proc Natl Acad Sci USA (1989); 86(10):3833-3737.

(56) References Cited

OTHER PUBLICATIONS

Patel, S. et al., "Impact of chimeric immune receptor extracellular protein domains on T cell function." Gene Ther (1999); 6(3): 412-419.
Perkins, et al., "Manufacturing an Enhanced Car T Cell Product By Inhibition of the PI3K/Akt Pathway During T Cell Expansion Results in Improved In Vivo Efficacy of Anti-BCMA Car T Cells." Blood (2015); 126(3): 1893.
Plückthun, A. "Antibodies from *Escherichia coli*." The Pharmacology of Monoclonal Antibodies. (eds. Rosenburg and Moore), Springer Berlin Heidelberg (1994); 113: 269-315.
Pomerantz, Joel L.,et al. "Structure-based design of transcription factors." Science (1995); 267.5194: 93-96.
Riechmann and Muyldermans, "Single domain antibodies: comparison of camel VH and camelised human VH domains", J Immunol Methods (1999); 231(1-2):25-38.
Rinfret, "Factors Affecting the Erythrocyte During Rapid Freezing and Thawing." Annals of the New York Academy of Sciences (1960); 85 (2): 576-594.
Ruella, M. and Kalos, M. "Adoptive immunotherapy for cancer." Immunological Reviews (2014); 257(1): 14-38.
Ryan, M. et al., "Virus-encoded proteinases of the picornavirus super-group." J Gen Virol. (1997); 78 (Pt 4): 699-723.
Sanchez, Eric, et al. "Serum B-cell maturation antigen is elevated in multiple myeloma and correlates with disease status and survival." British Journal of Haematology (2012); 158.6: 727-738.
Sather, B.B., et al. "Development of B-lineage Predominant Lentiviral Vectors for Use in Genetic Therapies for B Cell Disorders." Molecular Therapy (2011); 19(3): 515-525.
Schiemann, Barbara, et al. "An essential role for BAFF in the normal development of B cells through a BCMA-independent pathway." Science (2001); 293.5537: 2111-2114.
Shirasu and Kuroki, "Functional Design of Chimeric T-Cell Antigen Receptors for Adoptive Immunotherapy of Cancer: Architecture and Outcomes." Anticancer Research (2012); 32 (6): 2377-2383.
Shiratori, Y. et al., "Strategy of liver-directed gene therapy: present status and future prospects", Liver (1999); 19(4): 265-274.
Singh et al., "HER2-positive advanced breast cancer: optimizing patient outcomes and opportunities for drug development", British Journal of Cancer (2014); 111: 1888-1898.
Sloviter and Ravdin, "Recovery and Transfusion of Human Erythrocytes after freezing in Polyglycol Solutions." Nature (1962); 196: 899-900.
Smith-Arica and Bartlett, "Gene Therapy: Recombinant Adeno-associated Virus Vectors", Curr. Cardiol. Rep. (2001); 3: 43-49.
Somerville and Dudley, "Bioreactors get personal." OncoImmunology (2012); 1 (8): 1435-1437.
Soneoka, Yuko, et al. "A transient three-plasmid expression system for the production of high titer retroviral vectors." Nucleic Acids Research (1995); 23.4: 628-633.
Strayer, D.S., "Viral gene delivery", Expert Opinion on Investigational Drugs (1999); 8(12): 2159-2172.
Szymczak, Andrea L., et al. "Correction of multi-gene deficiency in vivo using a single'self-cleaving'2A peptide-based retroviral vector." Nature Biotechnology (2004); 22.5: 589-594.
Ten Berge, I. J. M., et al. "Selective expansion of a peripheral blood CD8+ memory T cell subset expressing both granzyme B and I-selectin during primary viral infection in renal allograft recipients." Transplantation Proceedings (1998); 30(8): 3975-3977.
Third Party Submission filed in U.S. Appl. No. 15/316,792, filed Feb. 23, 2018, 6 pages.
Thompson, Jeffrey S., et al. "BAFF binds to the tumor necrosis factor receptor-like molecule B cell maturation antigen and is important for maintaining the peripheral B cell population." Journal of Experimental Medicine (2000); 192.1: 129-136.
Thulé and Liu, "Regulated hepatic insulin gene therapy of STZ-diabetic rats", Gene Therapy (2000); 7: 1744-1752.
Tumaini, B., et al. "Simplified process for the production of anti-CD19-CAR-engineered T cells." Cytotherapy (2013); 15: 1406-1415.

Uchibori, et al., "CD269 (BCMA)-Specific CAR-Expressing T Cells Dramatically Eradicate Myeloma Cells from Bone Marrow of an Orthotopic Multiple Myeloma Mouse Model." Molecular Therapy (2016); Abstract 400, 24 (Supplement 1): p. S158-S159.
Urak, et al., "Ex vivo Akt inhibition promotes the generation of potent CD19CAR T cells for adoptive immunotherapy." Journal for ImmunoTherapy of Cancer (2017); 5(1): 26, 13 pages.
Van Der Waart, A.B., et al., "Akt Signalling Inhibition Promotes the Ex Vivo generation of Minor Histocompatibility Antigen-Specific CD8+ Memory Stem T Cells." Blood (2013); 122(21): 3269.
Van Der Waart, A.B., et al., "Inhibition of Akt signaling promotes the generation of superior tumor-reactive T cells for adoptive immunotherapy." Blood (2014); 124(23): 3490-3500.
Van Der Waart, A.B., et al., "Time to Akt Superior tumor-reactive T cells for adoptive immunotherapy." OncoImmunology (2015); 4(5): e1003016, 3 pages.
Vera, Juan, et al. "T lymphocytes redirected against the κ light chain of human immunoglobulin efficiently kill mature B lymphocyte-derived malignant cells." Blood (2006); 108.12: 3890-3897.
Wang, et al., "CS-1 Re-Directed Central Memory T Cell Therapy for Multiple Myeloma." Blood (2014); 124 (21): 1114.
Ward, et al., "Binding activities of a repertoire of single immunoglobulin variable domains secreted from *Escherichia coli*." Nature (1989); 341 (6242): 544-546.
Weigelt, et al., "Genomic determinants of the PI3K pathway inhibitor response in cancer." Frontiers in Oncology (2012), 2: Article V 109, pp. 1-16.
Wu and Kabat, "An analysis of the sequences of the variable regions of Bence Jones proteins and myeloma light chains and their implications for antibody complementarity", J Exp Med. (1970); 132(2): 211-250.
Wu, et al., "Over-expressing Akt in T cells to resist tumor immunosuppression and increase anti-tumor activity." BMC Cancer (2015); 15(1): 603, 10 pages.
Xu, Shengli, and Lam, Kong-Peng. "B-cell maturation protein, which binds the tumor necrosis factor family members BAFF and APRIL, is dispensable for humoral immune responses." Molecular and Cellular Biology (2001); 21.12: 4067-4074.
Xu et al., "The development of CAR design for tumor CAR-T cell therapy," Oncotarget, 2018, vol. 9, No. 17, pp. 13991-14004.
Xue L. et al., "The role of the PI3K-AKT kinase pathway in T-cell development beyond the beta checkpoint". Eur J Immunol., 2008, 38(11):3200-7.
Yang, N.S., "Gene Transfer into Mammalian Somatic Cells in Vivo", Critical Reviews in Biotechnology (1992); 12(4): 335-356.
Yang, Soo Young, et al. "A common pathway for T lymphocyte activation involving both the CD3-Ti complex and CD2 sheep erythrocyte receptor determinants." The Journal of Immunology (1986); 137.4: 1097-1100.
Yap, et al., "Preclinical Pharmacology, Antitumor Activity, and Development of Pharmacodynamic Markers for the Novel, Potent AKT Inhibitor CCT128930." Molecular Cancer Therapeutics (2011); 10(2): 360-371, (Published on-line First Dec. 29, 2010).
Yee, Jiing-Kuan, et al. "A general method for the generation of high-titer, pantropic retroviral vectors: highly efficient infection of primary hepatocytes." Proceedings of the National Academy of Sciences USA. (1994); 91.20: 9564-9568.
Zennou, V. et al., "HIV-1 genome nuclear import is mediated by a central DNA flap." Cell (2000); 101(2): 173-185.
Zhang, et al., "An NKp30-Based Chimeric Antigen Receptor Promotes T cell Effector Functions and Antitumor Efficacy In Vivo." The Journal of Immunology (2012); 189: 2290-2299 (prepublished online Jul. 30, 2012).
Zhong, Shi, et al. "Retroviral transduction of T-cell receptors in mouse T-cells." JoVE (Journal of Visualized Experiments) (2010); 44: e2307, 4 pages.
Zuckermann, Ronald N., et al. "Discovery of nanomolar ligands for 7-transmembrane G-protein-coupled receptors from a diverse N-(substituted) glycine peptoid library." Journal of Medicinal Chemistry (1994); 37.17: 2678-2685.
Zufferey et al., "Multiply attenuated lentiviral vector achieves efficient gene delivery in vivo", Nat Biotechnol. (1997), 15(9): 871-875.

(56) References Cited

OTHER PUBLICATIONS

Zufferey, R. et al., "Woodchuck hepatitis virus posttranscriptional regulatory element enhances expression of transgenes delivered by retroviral vectors." J Virol. (1999); 73(4): 2886-2892.

Zufferey, R. et al., "Self-Inactivating Lentivirus Vector for Safe and Efficient In Vivo Gene Delivery", J Virol (1998); 72(12): 9873-9880.

Berger et al., "CD28 costimulation and immunoaffinity-based selection efficiently generat primary gene-modified T cells for adoptive immunotherapy," Blood, Jan. 15, 2003, vol. 101, No. 2, pp. 476-484.

Bobisse et al., "Reprogramming T Lymphocytes for Melanoma Adoptive Immunotherapy by TCell Receptor Gene Transfer with Lentiviral Vectors," Cancer Research, Dec. 15, 2009; 69(24), pp. 9385-9394.

Brudno et al., "T cells genetically modified to express an anti-B-cell maturation antigen chimeric antigen receptor cause remissions of poor-prognosis relapsed multiple myeloma", Journal of Clinical Oncology 36(22): 2267 (2018).

Chono et al., "Engineering of CD19-CAR T Cells from Non-HodgkinLymphoma Patients in a Closed System in Combinationwith Retronectin/OKT3 Stimulation," Blood, Dec. 6, 2014, vol. 124, Issue 21, 6 pages.

Chono et al., "Optimization of lentiviral vector transduction into peripheral blood mononuclear cells in combination with the fibronectin fragment CH-296 stimulation," J. Biochem., Nov. 23, 2010, 149(3), pp. 285-292.

Cieri et al., "IL-7 and IL-15 instruct the generation of human memory stem T cells from naive precursors," Blood, Jan. 24, 2013, 12 pages.

Clarke et al., "Improved Post-Thaw Recovery of Peripheral Blood Stem/Progenitor Cells Using a Novel Intracellular-like Cryopreservation Solution," Cytotherapy, 2009, 11(4): 472-479.

Copy of extract from ThermoFisher Website page, Dynabeads cell isolation and expansion support—getting started, 1 page.

Dai et al., "Human Immunodeficiency Virus Integrates Directly into Naïve Resting CD4+ T Cells but Enters Naïve Cells Less Efficiently than Memory Cells," Journal of Virology, May 2009, pp. 4528-4537.

Di Ianni et al., "Immunomagnetic isoloation of CD4+CD25+ FoxP3+ natural T regulatory lymphocytes for clinical applications," Jan. 9, 2009, British Society for Immunology, Clinical and Experimental Immunology, 156: pp. 246-253.

Dotti, et al., "Design and development of therapies using chimeric antigen receptor- expressing T cells." Immunol Rev. (2014); 257 (1): 107-126, 35 pages. First published: Dec. 13, 2013.

European Application No. EP 15783117.3, Notice of Opposition dated Jan. 19, 2021, 37 pages.

European Application No. EP 15783117.3, Notice of Opposition dated Jan. 21, 2021, 28 pages.

European Application No. EP 15783117.3, Notice of Opposition dated Jan. 22, 2021, 41 pages.

Extended European Search Report for EP Application No. 19218258.2 dated Jun. 26, 2020, 7 pages.

Extended European Search Report for EP Application No. 20205511.7 dated May 6, 2021, 13 pages.

Extended European Search Report for European Application No. EP20784056.2 dated Apr. 6, 2023, 14 pages.

Extract from Signal Peptide Database, Jun. 10, 2010, 3 pages.

Ficoll-Paque manual, GE Healthcare Life Sciences, Isolation of mononuclear cells, Methodology and applications, Aug. 2014, 20 pages.

Field et al., "Comparison of Lentiviral and Sleeping Beauty Mediated al3 T Cell Receptor Gene Transfer," PLoS ONE, 8(6), Jun. 28, 2013, 9 pages.

Gattinoni, L., et al., "Moving T memory stem cells to the clinic," Blood, Jan. 24, 2013, vol. 121, No. 4, pp. 567-568.

Guest et al., "Definition and application of good manufacturing process-compliant production of CEA-specific chimeric antigen receptor expressing T-cells for phase I/II clinical trial," Cancer Immunol Immunother (2014) 63: 133-145, Nov. 5, 2013; Supplementary Materials published with Guest et al. (2014) Cancer Immunol. Immunother. 63: 133-145.

Han et al., "Polyfunctional responses by human T cells result from sequential release of cytokines," PNAS, Jan. 31, 2012, vol. 109, No. 5, pp. 1607-1612.

Hillerdal et al., "Systemic treatment with CAR-engineered T cells against PSCA delays subcutaneous tumor growth and prolongs survival of mice," BMC Cancer, Jan. 8, 2014, 14:30, 9 pages.

Ho Y.J., et al., "Promoter usage regulating the surface density of CAR molecules may modulate the kinetics of CAR-T cells in vivo," Molecular Therapy, Methods & Clinical Development, Jun. 11, 2021, pp. 237-246, doi: 10.1016/j.omtm.2021.03.007. eCollection 2021.

Iliopoulou et al., "Increased Frequency of CD4+ Cells Expressing CD161 in Cancer Patients," Clinical Cancer Research, Dec. 1, 2006, 12(23), pp. 6901-6909.

June et al., "Engineering lymphocyte subsets: tools, trials and tribulations," Nature Reviews Immunology 9(10):704-716, Oct. 2009.

Kutner et al., "Simplified production and concentration of HIV-1-based lentiviral vectors using HYPERFlask vessels and anion exchange membrane chromatography", BMC Biotechnol. (2009); 9:10. p. 1-7.

Liu et al. "Design of polydactyl zinc-finger proteins for unique addressing within complex genomes." Proceedings of the National Academy of Sciences (1997); 94.11: 5525-5530.

Mallone et al., "Isolation and preservation of peripheral blood mononuclear cells for analysis of islet antigen-reactive T cell responses: position statement of the T-Cell Workshop Committee of the Immunology of Diabetes Society," Clin Exp Immunol. Jan. 2011; 163(1):33-49.

Mei et al., "Blood-borne human plasma cells in steady state are derived from mucosal immune responses," Blood, Mar. 12, 2009, vol. 113, No. 11, pp. 2461-2469.

Min et al., "Molecular Targeted Tumor Therapy," Jinan: Shandong Science and Technology Press, Mar. 2009, 6 pages.

Munshi et al., "Idecabtagene Vicleucel in Relapsed and Refractory Multiple Myeloma", New England Journal of Medicine, 2021; 384:705-716.

Notice Regarding the General Guideline Relating to Clinical Evaluation of New Pharmaceuticals, Yakushinyako No. 43, Notice from the Chief of the Section of New Pharmaceuticals, the Department of Pharmaceutical Affair, the Ministry of Health, Labour and Welfare to the chief of the Main Department of Sanitation Control of each prefecture, 1992, pp. 1-12.

Pouw et al., "TCR gene-engineered T cell: Limited T cell activation and combined use of IL-15 and IL-21 ensure minimal differentiation and maximal antigen-specificity," Molecular Immunology, Feb. 19, 2010, 47, pp. 1411-1420.

Product Leaflet, Dynabeads ® CD3/CD28, 2018, 2 pages.

Raje et al., "Anti-BCMA CAR T-Cell Therapy bb2121 in Relapsed or Refractory Multiple Myeloma", New England Journal of Medicine, 2019; 380: 1726-1737.

Rodriguez-Otero et al., "Ide-cel or Standard Regimens in Relapsed and Refractory Multiple Myeloma", New England Journal of Medicine, 2023; 388: 1002-1014.

RosetteSep Data Sheet, 2018, 3 pages.

Ryan et al., Antibody targeting of B-cell maturation antigen on malignant plasma cells, Mot Cancer Ther, Nov. 2007, vol. 6, No. 11, pp. 3009-3018.

Schuler et al., "Separation of human CD4+CD39+ T cells by magnetic beads reveals two phenotypically and functionally different subsets," J. Immunol. Methods, Jun. 30, 2011, 369(1- 2), 59-68, 19 pages.

Shi et al., "Chimeric antigen receptor for adoptive immunotherapy of cancer: latest research and future prospects," Molecular Cancer 2014, 13:219, 8 pages.

Somerville et al., "Clinical scale rapid expansion of lymphocytes for adoptive cell transfer therapy in the WAVE® bioreactor," Journal of Translational Medicine, Apr. 4, 2012, 10:69, 11 pages.

Supplementary Materials published with Milone et al. (2009) Mol. Ther. 17(8): 1453-1464.

(56) References Cited

OTHER PUBLICATIONS

Tumeh et al., "The impact of ex vivo clinical grade activation protocols on human T cell phenotype and function for the generation of genetically modified cells for adoptive cell transfer therapy," J Immunother., Oct. 2010, 33(8):759-68.

Verhoeyen et al., "Lentiviral Vector Gene Transfer Into Human T Cells," Methods in Molecular Biology, Methods and Protocols, 2009, vol. 506, pp. 97-114.

Washington et al., "Innate Immune Factors Are Expressed among Peripheral BloodCD34 + HSCs, Are Induced upon Exposure to Lentiviral Vectors and May Limit Transduction Efficiency," Blood, Nov. 16, 2007, vol. 110, Issue 11, 6 pages.

Xu et al., "Closely related T-memory stem cells correlate with in vivo expansion of CAR.CD19-T cells and are preserved by IL-7 and IL-15," Blood, Jun. 12, 2014, vol. 123, No. 24.

Xue et al., "ZSTK474, a novel P13K inhibitor, modulates human CD14+ monocyte-derived dendritic cell functions and suppresses experimental autoimmune encephalomyelitis," J Mot Med, May 22, 2014, 92:1057-1068.

Yang, "In vitro generated anti-tumor T lymphocytes exhibit distinct subsets mimicking in vivo antigen-experienced cells", Cancer Immunol Immunother (2011) 60:739-749.

Zhang et al., "Anti-melanoma activity of T cells redirected with a TOR-like chimeric antigen receptor," Scientific Reports, Jan. 6, 2014, 4: 3571, 8 pages.

Amaishi et al., "A Novel Vector for CAR-T Cells with Enhanced Antitumor Response and Reduced Risk of CRS and ICANS", Molecular Therapy 31(4) Supp 1, pp. 472. Abstract No. 971 (2023).

Amantea et al., "Oxysterol-Induced Osteogenic Differentiation of Marrow Stromal Cells is Regulated by Dkk-1 Inhibitable and PI3-Kinase Mediated Signaling", Journal of Cellular Biochemistry, Oct. 1, 2008, vol. 105, No. 2, pp. 424-436.

Extended European Search Report for EP Application No. 21187802.0 dated Feb. 18, 2022, 14 pages.

Extended European Search Report for EP Application No. 21198992.6 dated Apr. 20, 2022, 15 pages.

International Preliminary Report on Patentability for International Application No. PCT/US2017/59989 dated May 7, 2019.

International Search Report and Written Opinion for International Application No. PCT/US2020/026300, dated Jul. 9, 2020, 21 pages.

Jakubikova et al. "Role of PI3K/Akt and MEK/ERK Signaling Pathways in Sulforaphane- and Erucin-Induced Phase II Enzymes and MRP2 Transcription, G2/M Arrest and Cell Death in Caco-2 Cells," Biochemical Pharmacology, Jun. 1, 2005, vol. 69, No. 11, pp. 1543-1552.

Morgan et al., "Engineering CAR-T Cells for Improved Function Against Solid Tumors", Frontiers in Immunology, Oct. 29, 2018, vol. 9, Art. 2493, pp. 1-11.

\* cited by examiner

ANTI-BCMA CAR T CELL COMPOSITIONS

CROSS REFERENCE TO RELATED APPLICATIONS

This application is a U.S. national phase application of International PCT Patent Application No. PCT/US2017/059989, filed on Nov. 3, 2017, which claims the benefit under 35 U.S.C. § 119(e) of U.S. Provisional Application No. 62/514,401, filed Jun. 2, 2017, and U.S. Provisional Application No. 62/417,840, filed Nov. 4, 2016, each of which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BLBD_079_02WO_ST25.txt. The text file is 27 KB, was created on Nov. 3, 2017, and is being submitted electronically via EFS-Web, concurrent with the filing of the specification.

BACKGROUND

Technical Field

The present invention relates to improved compositions and methods for treating B cell related conditions. More particularly, the invention relates to improved compositions comprising therapeutic doses of anti-BCMA chimeric antigen receptor (CAR) T cells to treat relapsed/refractory multiple myeloma.

Description of the Related Art

Chimeric Antigen Receptor (CAR) T-cells are molecules that combine antibody-based specificity for a desired antigen with a T cell receptor-activating intracellular domain to generate a chimeric protein that exhibits a specific anticancer immune activity. CARs endow a patient's own T cells with the ability to recognize and kill cancer cells directly. CAR T cell technology has developed rapidly, but has yet to realize its therapeutic potential. Several obstacles remain to the clinical application of CAR T cells to hematological malignancies.

Most CAR T cell therapies applied to hematological malignancies are associated with cytokine release syndrome (CRS) or cytokine storm. CRS is specific for adoptive cellular immunotherapies, manifests with septic shock-like symptoms, and may ultimately result in patient death. In fact, a number of clinical trials were temporarily suspended by the FDA due to CRS-related deaths in CAR T-cell trials. CRS can be rapid, unpredictable and currently, there is no consensus on prevention and management of CRS. However, one characteristic that contributes to CRS is the therapeutic cell dose of CAR T cells.

CAR T cells are "living drugs" that have the ability to multiply in vivo—after infusion and home to bone marrow. For example, in a seminal case study from UPenn, published in 2011, as low as $1.5 \times 10^5$ CART cells, given to chronic lymphocytic leukemia (CLL) patients, expanded more than 1000 times in vivo over time. Thus, CART cell therapy presents a unique set of challenges with respect to dosing. There is no uniform consensus on CAR T cell infusion dosage and influence factors, including tumor load, efficacy and side effects. Small dose infusions may not obtain the ideal curative effect, but may instead induce tumor antigen deletion, and antigen escape. Large dose infusions and serious tumor load will increase CRS and tumor lysis syndrome. Because it is a living drug, determining the correct therapeutic dose is unpredictable. Conventional drug-body interaction concepts of pharmacodynamics and pharmacokinetics can't readily be applied to CAR T cell therapy because CAR T cells are a dynamic, living, and persistent drug.

Some challenges to dose selection include, but are not limited to, the paucity of correlative animal models, first in human products have limited "a priori" information, in-vivo expansion of humans cell is unpredictable, the limitations in "borrowing" safety data from first generation CAR T products, extrapolating safety data from related products (TILs, "similar" TCR redirected cells, "similar" class of CAR T product, and extrapolating safety data using the same product in histologically different tumor type(s).

Accordingly, current approaches to CAR T cell dosing do not appear to be sufficiently mature to predict therapeutically effective CAR T cell dose among T cells harboring different CARs for use in the same indication and among the same CAR T cells for use in different indications.

BRIEF SUMMARY

The invention generally provides improved anti-BCMA CAR T cell compositions and methods of using the same to treat relapsed/refractory multiple myeloma.

In various embodiments, a composition is contemplated comprising a therapeutically effective amount of anti-B cell maturation antigen (BCMA) chimeric antigen receptor (CAR) T cells, wherein the therapeutically effective amount is greater than about $5.0 \times 10^7$ anti-BCMA CAR T cells, and the anti-BCMA CAR comprises the amino acid sequence set forth in SEQ ID NO: 9.

In particular embodiments, the composition further comprises a pharmaceutically acceptable carrier.

In certain embodiments, the composition is formulated in a solution comprising 50:50 PlasmaLyte A to CryoStor CS10.

In various embodiments, the therapeutically effect amount is at least about $15.0 \times 10^7$ anti-BCMA CAR T cells.

In particular embodiments, the therapeutically effect amount is at least about $45.0 \times 10^7$ anti-BCMA CAR T cells.

In some embodiments, the therapeutically effect amount is at least about $80.0 \times 10^7$ anti-BCMA CAR T cells.

In certain embodiments, the therapeutically effect amount is at least about $12.0 \times 10$ anti-BCMA CAR T cells.

In particular embodiments, the therapeutically effect amount is between about $5.0 \times 10^7$ anti-BCMA CART cells and about $15.0 \times 10^7$ anti-BCMA CART cells.

In various embodiments, the therapeutically effect amount is between about $5.0 \times 10^7$ anti-BCMA CAR T cells and about $45.0 \times 10^7$ anti-BCMA CAR T cells.

In some embodiments, the therapeutically effect amount is between about $5.0 \times 10^7$ anti-BCMA CAR T cells and about $80.0 \times 10^7$ anti-BCMA CAR T cells.

In particular embodiments, the therapeutically effect amount is between about $5.0 \times 10^7$ anti-BCMA CART cells and about $12.0 \times 10^8$ anti-BCMA CART cells.

In certain embodiments, the therapeutically effect amount is between about $15.0 \times 10^7$ anti-BCMA CAR T cells and about $45.0 \times 10^7$ anti-BCMA CAR T cells.

In some embodiments, the therapeutically effect amount is between about $15.0 \times 10^7$ anti-BCMA CAR T cells and about $80.0 \times 10^7$ anti-BCMA CAR T cells.

In various embodiments, the therapeutically effect amount is between about $15.0 \times 10^7$ anti-BCMA CART cells and about $12.0 \times 10^8$ anti-BCMA CART cells.

In particular embodiments, the anti-BCMA CAR T cells are transduced with a lentiviral vector encoding the anti-BCMA CAR.

In certain embodiments, the lentiviral vector copy number (VCN) is about 2.0 copies per anti-BCMA CAR T cell.

In certain embodiments, the lentiviral vector is a human immunodeficiency virus 1 (HIV-1) vector.

In particular embodiments, a pharmaceutical composition is contemplated comprising a population of T cells transduced with a lentivirus encoding an anti-BCMA CAR, wherein population of T cells comprises greater than about $5.0 \times 10^7$ anti-BCMA CART cells, and the anti-BCMA CAR comprises the amino acid sequence set forth in SEQ ID NO: 9.

In some embodiments, the composition further comprising a therapeutically acceptable carrier.

In various embodiments, the composition comprises at least about $15.0 \times 10^7$ anti-BCMA CAR T cells.

In particular embodiments, the composition comprises at least about $45.0 \times 10^7$ anti-BCMA CAR T cells.

In some embodiments, the composition comprises at least about $80.0 \times 10^7$ anti-BCMA CAR T cells.

In certain embodiments, the composition comprises at least about $12.0 \times 10$ anti-BCMA CAR T cells.

In various embodiments, the composition comprises about $15.0 \times 10^7$ anti-BCMA CAR T cells.

In particular embodiments, the composition comprises about $45.0 \times 10^7$ anti-BCMA CAR T cells.

In some embodiments, the composition comprises about $80.0 \times 10^7$ anti-BCMA CAR T cells.

In certain embodiments, the composition comprises about $12.0 \times 10$ anti-BCMA CAR T cells.

In particular embodiments, the composition comprises between about $5.0 \times 10^7$ anti-BCMA CART cells and about $15.0 \times 10^7$ anti-BCMA CART cells.

In various embodiments, the composition comprises between about $5.0 \times 10^7$ anti-BCMA CART cells and about $45.0 \times 10^7$ anti-BCMA CART cells.

In particular embodiments, the composition comprises between about $5.0 \times 10^7$ anti-BCMA CART cells and about $80.0 \times 10^7$ anti-BCMA CART cells.

In some embodiments, the composition comprises between about $5.0 \times 10^7$ anti-BCMA CART cells and about $12.0 \times 10^8$ anti-BCMA CART cells.

In various embodiments, the composition comprises between about $15.0 \times 10^7$ anti-BCMA CART cells and about $45.0 \times 10^7$ anti-BCMA CART cells.

In certain embodiments, the composition comprises between about $15.0 \times 10^7$ anti-BCMA CART cells and about $80.0 \times 10^7$ anti-BCMA CART cells.

In some embodiments, the composition comprises between about $15.0 \times 10^7$ anti-BCMA CART cells and about $12.0 \times 10^8$ anti-BCMA CART cells.

In particular embodiments, the T cells comprise CD8+ T cells.

In various embodiments, a method of treating a subject that has been diagnosed with relapsed/refractory multiple myeloma is provided comprising administering the subject a composition contemplated herein.

In particular embodiments, a method of treating a subject that has relapsed/refractory multiple myeloma is provided, comprising administering the subject the composition contemplated herein.

In certain embodiments, the composition is administered in a single dose.

In certain embodiments, the composition is intravenously administered.

In some embodiments, the multiple myeloma was refractory to at least three treatment regimens, including a proteasome inhibitor and an immunomodulatory agent, prior to the administration of the composition.

In particular embodiments, the multiple myeloma was double-refractory to one or more treatment regimens, prior to the administration of the composition.

In some embodiments, the subject was treated with daratumumab, lenalidomide, pomalidomide, bortezomib, and/or carfilzomib, prior to the administration of the composition.

In certain embodiments, the subject received an autologous hematopoietic stem cell transplant, prior to the administration of the composition.

In particular embodiments, the subject was lymphodepleted with cyclophosphamide 300 mg/m$^2$ and fludarabine 30 mg/m$^2$.

BRIEF DESCRIPTION OF THE SEQUENCE IDENTIFIERS

Figure 1:
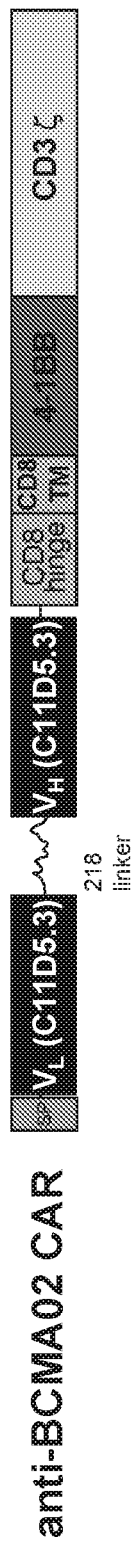
FIG. 1 shows a schematic of a murine B cell maturation antigen (muBCMA) CAR construct.

SEQ ID NOs: 1-3 set forth amino acid sequences of exemplary light chain CDR sequences for BCMA CARs contemplated herein.

SEQ ID NOs: 4-6 set forth amino acid sequences of exemplary heavy chain CDR sequences for BCMA CARs contemplated herein.

SEQ ID NO: 7 sets forth an amino acid sequence of an exemplary light chain sequences for BCMA CARs contemplated herein.

SEQ ID NO: 8 sets forth an amino acid sequence of an exemplary heavy chain sequences for BCMA CARs contemplated herein.

SEQ ID NO: 9 sets forth an amino acid sequence of an exemplary BCMA CAR contemplated herein.

SEQ ID NO: 10 set forth a polynucleotide sequence that encode an exemplary BCMA CAR contemplated herein.

SEQ ID NO: 11 sets forth the amino acid sequence of human BCMA.

SEQ ID NO: 12-22 set for the amino acid sequence of various linkers.

SEQ ID NOs: 23-35 set for the amino acid sequence of protease cleavage sites and self-cleaving polypeptide cleavage sites.

SEQ ID NO: 36 sets for the polynucleotide sequence of a vector encoding a BCMA CAR.

DETAILED DESCRIPTION

A. Overview

Significant challenges exist in the art to predicting a therapeutically effective CAR T cell dose with respect to a particular CAR and its target indication. The present disclosure generally relates to improved anti-BCMA CAR T cell compositions and methods for treating relapsed/refractory multiple myeloma.

B cell maturation antigen (BCMA, also known as CD269 or tumor necrosis factor receptor superfamily, member 17; TNFRSF17 is a member of the tumor necrosis factor receptor superfamily (see, e.g., Thompson et al., *J Exp. Medicine*, 192(1): 129-135, 2000, and Mackay et al., *Annu. Rev. Immunol*, 21: 231-264, 2003. BCMA binds B-cell activating factor (BAFF) and a proliferation inducing ligand (APRIL) (see, e.g., Mackay et al., 2003 and Kalled et al., *Immunological Reviews*, 204: 43-54, 2005). Among nonmalignant cells, BCMA has been reported to be expressed mostly in plasma cells and subsets of mature B-cells (see, e.g., Laabi et al., *EMBO J.*, 77(1): 3897-3904, 1992; Laabi et al., *Nucleic Acids Res.*, 22(7): 1147-1154-1994; Kalled et al., 2005; O'Connor et al., *J Exp. Medicine*, 199(1): 91-97, 2004; and Ng et al., *J Immunol.*, 73(2): 807-817, 2004. Mice deficient in BCMA are healthy and have normal numbers of B cells, but the survival of long-lived plasma cells is impaired (see, e.g., O'Connor et al., 2004; Xu et al., *Mol. Cell. Biol*, 21(12): 4067-4074, 2001; and Schiemann et al., *Science*, 293(5537): 2 111-21 14, 2001). BCMA RNA has been detected universally in multiple myeloma cells and in other lymphomas, and BCMA protein has been detected on the surface of plasma cells from multiple myeloma patients by several investigators (see, e.g., Novak et al., *Blood*, 103(2): 689-694, 2004; Neri et al., *Clinical Cancer Research*, 73(19): 5903-5909, 2007; Bellucci et al., *Blood*, 105(10): 3945-3950, 2005; and Moreaux et al., *Blood*, 703(8): 3148-3157, 2004.

In various embodiments, the improved adoptive cell therapy compositions contemplated herein comprise therapeutically effective doses of anti-BCMA CAR T cells that unexpectedly expand and elicit clinical responses in vivo, in the absence of severe cytokine release syndrome CRS.

In particular embodiments, the improved compositions comprising therapeutically effective doses of anti-BCMA CAR T cells contemplated herein are used to treat relapsed/refractory multiple myeloma.

The practice of the invention will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology*; as well as monographs in journals such as *Advances in Immunology*.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein. For the purposes of the present invention, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 20%, 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±20%, ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

"Polypeptide," "polypeptide fragment," "peptide" and "protein" are used interchangeably, unless specified to the contrary, and according to conventional meaning, i.e., as a sequence of amino acids. Polypeptides are not limited to a specific length, e.g., they may comprise a full-length protein sequence or a fragment of a full length protein, and may include post-translational modifications of the polypeptide, for example, glycosylations, acetylations, phosphorylations and the like, as well as other modifications known in the art, both naturally occurring and non-naturally occurring. In various embodiments, the CAR polypeptides contemplated herein comprise a signal (or leader) sequence at the N-terminal end of the protein, which co-translationally or post-translationally directs transfer of the protein. Illustrative examples of suitable signal sequences useful in CARs disclosed herein include, but are not limited to the IgG1 heavy chain signal sequence and the CD8a signal sequence. Polypeptides can be prepared using any of a variety of well-known recombinant and/or synthetic techniques. Polypeptides contemplated herein specifically encompass the CARs of the present disclosure, or sequences that have deletions from, additions to, and/or substitutions of one or more amino acid of a CAR as disclosed herein. In particular embodiments, the term "polypeptide" further includes variants, fragments, and fusion polypeptides An "isolated peptide" or an "isolated polypeptide" and the like, as used herein, refer to in vitro isolation and/or purification of a peptide or polypeptide molecule from a cellular environment, and from association with other components of the cell, i.e., it is not significantly associated with in vivo substances. Similarly, an "isolated cell" refers to a cell that has been obtained from an in vivo tissue or organ and is substantially free of extracellular matrix.

Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. For example, in particular embodiments, it may be desirable to improve the binding affinity and/or other biological properties of the CARs by introducing one or more substitutions, deletions, additions and/or insertions into a binding domain, hinge, TM domain, co-stimulatory signaling domain or primary signaling domain of a CAR polypeptide. Preferably, polypeptides of the invention include polypeptides having at least about 65%, 70%, 75%, 85%, 90%, 95%, 98%, or 99% amino acid identity thereto.

Polypeptides include "polypeptide fragments." Polypeptide fragments refer to a polypeptide, which can be monomeric or multimeric and that has an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long.

Fusion polypeptides and fusion proteins refer to a polypeptide having at least two, three, four, five, six, seven, eight, nine, or ten or more polypeptide segments.

As used herein, the terms "polynucleotide" or "nucleic acid" refers to messenger RNA (mRNA), RNA, genomic RNA (gRNA), plus strand RNA (RNA(+)), minus strand RNA (RNA(−)), genomic DNA (gDNA), complementary DNA (cDNA) or recombinant DNA. Polynucleotides include single and double stranded polynucleotides. Preferably, polynucleotides of the invention include polynucleotides or variants having at least about 50%, 55%, 60%, 65%, 70%, 75%, 80%, 85%, 90%, 95%, 96%, 97%, 98%, 99% or 100% sequence identity to any of the reference sequences described herein (see, e.g., Sequence Listing), typically where the variant maintains at least one biological activity of the reference sequence. In various illustrative embodiments, the present invention contemplates, in part, polynucleotides comprising expression vectors, viral vectors, and transfer plasmids, and compositions, and cells comprising the same.

As used herein, "isolated polynucleotide" refers to a polynucleotide that has been purified from the sequences which flank it in a naturally-occurring state, e.g., a DNA fragment that has been removed from the sequences that are normally adjacent to the fragment. An "isolated polynucleotide" also refers to a complementary DNA (cDNA), a recombinant DNA, or other polynucleotide that does not exist in nature and that has been made by the hand of man.

The "control elements" or "regulatory sequences" present in an expression vector are those non-translated regions of the vector—origin of replication, selection cassettes, promoters, enhancers, translation initiation signals (Shine Dalgarno sequence or Kozak sequence) introns, a polyadenylation sequence, 5' and 3' untranslated regions—which interact with host cellular proteins to carry out transcription and translation. Such elements may vary in their strength and specificity. Depending on the vector system and host utilized, any number of suitable transcription and translation elements, including ubiquitous promoters and inducible promoters may be used.

An "endogenous" control sequence is one which is naturally linked with a given gene in the genome. An "exogenous" control sequence is one which is placed in juxtaposition to a gene by means of genetic manipulation (i.e., molecular biological techniques) such that transcription of that gene is directed by the linked enhancer/promoter. A "heterologous" control sequence is an exogenous sequence that is from a different species than the cell being genetically manipulated.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide.

The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

The term "vector" is used herein to refer to a nucleic acid molecule capable transferring or transporting another nucleic acid molecule.

The term "lentiviral vector" refers to a viral vector or plasmid containing structural and functional genetic elements, or portions thereof, including LTRs that are primarily derived from a lentivirus.

In particular embodiments, the terms "lentiviral vector," "lentiviral expression vector" may be used to refer to lentiviral transfer plasmids and/or infectious lentiviral particles. Where reference is made herein to elements such as cloning sites, promoters, regulatory elements, heterologous nucleic acids, etc., it is to be understood that the sequences of these elements are present in RNA form in the lentiviral particles and are present in DNA form in the DNA plasmids.

"Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication. Self-inactivation is preferably achieved through in the introduction of a deletion in the U3 region of the 3' LTR of the vector DNA, i.e., the DNA used to produce the vector RNA. Thus, during reverse transcription, this deletion is transferred to the 5' LTR of the proviral DNA. In particular embodiments, it is desirable to eliminate enough of the U3 sequence to greatly diminish or abolish altogether the transcriptional activity of the LTR, thereby greatly diminishing or abolishing the production of full-length vector RNA in transduced cells. In the case of HIV based lentivectors, it has been discovered that such vectors tolerate significant U3 deletions, including the removal of the LTR TATA box (e.g., deletions from ~418 to −18), without significant reductions in vector titers.

C. Anti-BCMA Chimeric Antigen Receptors

In various embodiments, genetically engineered receptors that redirect cytotoxicity of T cells toward BCMA expressing cells are provided. These genetically engineered receptors referred to herein as anti-BCMA chimeric antigen receptors (CARs).

Anti-BCMA CARs contemplated in particular embodiments, comprise a signal peptide, an anti-BCMA scFv, a CD8a hinge domain, a CD8a transmembrane domain, a 4-1BB co-stimulatory domain, and a CD3 primary signaling domain.

"Single-chain Fv" or "scFv" antibody fragments comprise the VH and VL domains of antibody, wherein these domains are present in a single polypeptide chain and in either orientation (e.g., VL-VH or VH-VL). Generally, the scFv polypeptide further comprises a polypeptide linker between the VH and VL domains which enables the scFv to form the desired structure for antigen binding.

"VH" or "VH" refer to the variable region of an immunoglobulin heavy chain. "VL" or "VL" refer to the variable region of an immunoglobulin light chain. In various embodiments, the scFv comprises a light chain sequence set forth in SEQ ID NO: 7 and a heavy chain sequence set forth in SEQ ID NO: 8.

Light and heavy chain variable regions contain three hypervariable regions, also called "complementarity-determining regions" or "CDRs." In particular embodiments, the scFv light chain comprises the CDRL1-3 sequences set forth in SEQ ID NOs: 1-3, and the scFv heavy chain comprises the CDRH1-3 sequences set forth in SEQ ID NOs: 4-6.

In certain embodiments, the CARs contemplated herein may comprise linker residues between the various domains, e.g., added for appropriate spacing and conformation of the molecule. In particular embodiments, the linker comprises the following amino acid sequence: GSTSGSGKPGSGEG-STKG (SEQ ID NO: 22) (Cooper et al., *Blood*, 101(4): 1637-1644 (2003)).

In particular embodiments, the hinge domain comprises a CD8a hinge region.

The "transmembrane domain" is the portion of the CAR that fuses the extracellular binding portion and intracellular signaling domain and anchors the CAR to the plasma membrane of the T cell. In particular embodiments, the transmembrane domain comprises a CD8a transmembrane region.

In particular embodiments, a CAR contemplated herein comprises a "co-stimulatory signaling domain" and a "primary signaling domain." As used herein, the term, "co-stimulatory signaling domain," or "co-stimulatory domain," refers to an intracellular signaling domain of a co-stimulatory molecule. Primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs. In particular embodiments, the anti-BCMA CAR comprises a CD137 co-stimulatory signaling domain and a CD3 primary signaling domain.

In preferred embodiments, the anti-BCMA CAR comprises the amino acid sequence set forth in SEQ ID NO: 9.

In particular embodiments, a polynucleotide encoding an anti-BCMA CAR polypeptides set forth in SEQ ID NO: 9 is provided.

The polynucleotides contemplated in particular embodiments, regardless of the length of the coding sequence itself, may be combined with other DNA sequences, such as promoters and/or enhancers, untranslated regions (UTRs), signal sequences, Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, with the total length preferably being limited by the ease of preparation and use in the intended recombinant DNA protocol.

In particular embodiments, a vector encoding an anti-BCMA CAR contemplated herein is a viral vector, will include exogenous, endogenous, or heterologous control sequences such as promoters and/or enhancers.

In a particular embodiment, the vector comprises a myeloproliferative sarcoma virus enhancer, negative control region deleted, dl587rev primer-binding site substituted (MND) promoter (Challita et al., *J Virol.* 69(2):748-55 (1995)) operably linked to a polynucleotide encoding an anti-BCMA CAR contemplated herein.

In particular embodiments, a cell (e.g., a T cell) is transduced with a retroviral vector, e.g., a lentiviral vector, encoding an anti-BCMA CAR contemplated herein. In preferred embodiments, the lentiviral vector is HIV (human immunodeficiency virus; including HIV type 1). In particular preferred embodiments, the lentiviral vectors is a SIN HIV-1 vector.

D. Anti-BCMA CAR T Cells

The present disclosure contemplates, in particular embodiments, T cells comprising an anti-BCMA CAR, e.g., anti-BCMA CAR T cells. The terms "T cell" or "T lymphocyte" are art-recognized and are intended to include thymocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; $CD4^+$ T cell) $CD4^+$ T cell, a cytotoxic T cell (CTL; $CD8^+$ T cell), $CD4^+CD8^+$ T cell, $CD4^-CD8^-$ T cell, or any other subset of T cells. Other illustrative populations of T cells suitable for use in particular embodiments include naïve T cells and memory T cells.

T cells of the invention can be autologous/autogeneic ("self") or non-autologous ("non-self" e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells of the invention are allogeneic.

T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation. In one embodiment, cells from the circulating blood of an individual are obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing. The cells can be washed with PBS or with another suitable solution that lacks calcium, magnesium, and most, if not all other, divalent cations. As would be appreciated by those of ordinary skill in the art, a washing step may be accomplished by methods known to those in the art, such as by using a semiautomated flow-through centrifuge. For example, the Cobe 2991 cell processor, the Baxter CytoMate, or the like. After washing, the cells may be resuspended in a variety of biocompatible buffers or other saline solution with or without buffer. In certain embodiments, the undesirable components of the apheresis sample may be removed in the cell directly resuspended culture media.

T cells can be genetically modified following isolation using known methods, or the T cells can be activated and expanded (or differentiated in the case of progenitors) in vitro prior to being genetically modified. In a particular embodiment, the T cells are genetically modified with the chimeric antigen receptors contemplated herein (e.g., transduced with a viral vector comprising a nucleic acid encoding a CAR) and then are activated and expanded in vitro. In various embodiments, T cells can be activated and expanded before or after genetic modification to express a CAR.

In one embodiment, T cells expressing an anti-BCMA CAR are cryopreserved such that the cells remain viable upon thawing. As used herein, "cryopreserving," refers to the preservation of cells by cooling to sub-zero temperatures, such as (typically) 77 K or −196° C. (the boiling point of liquid nitrogen). Cryoprotective agents are often used at sub-zero temperatures to prevent the cells being preserved from damage due to freezing at low temperatures or warming to room temperature. Cryopreservative agents and optimal cooling rates can protect against cell injury. Cryoprotective agents which can be used include but are not limited to dimethyl sulfoxide (DMSO) (Lovelock and Bishop, Nature, 1959; 183: 1394-1395; Ashwood-Smith, Nature, 1961; 190: 1204-1205), glycerol, polyvinylpyrrolidine (Rinfret, Ann. N.Y. Acad. Sci., 1960; 85: 576), and polyethylene glycol (Sloviter and Ravdin, Nature, 1962; 196: 48). The preferred cooling rate is 1° to 3° C./minute. After at least two hours, the T cells have reached a temperature of −80° C. and can be placed directly into liquid nitrogen (−196° C.) for permanent storage such as in a long-term cryogenic storage vessel.

E. Compositions and Formulations

The compositions contemplated herein comprise a therapeutically effective amount of anti-BCMA CAR T cells. Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

In particular embodiments, compositions comprise an amount, and more preferably a therapeutically effective amount, of anti-BCMA CAR-expressing T cells contemplated herein.

As used herein, the term "amount" or "dose" refers to "an amount effective," "a dose effective," "an effective amount," or "an effective dose" of an anti-BCMA CAR T cell sufficient to achieve a beneficial or desired prophylactic or therapeutic result, including clinical results.

A "therapeutically effective amount" or "therapeutically effective dose" of an anti-BCMA CAR T cell is also one in which any toxic or detrimental effects of an anti-BCMA CAR T cell, e.g., CRS, are outweighed by the therapeutically beneficial effects. The term "therapeutically effective amount" includes an amount that is effective to "treat" a subject (e.g., a patient). In one embodiment, the therapeutically effective dose is the minimal effective dose (MED) of anti-BCMA CART cells to treat multiple myeloma in a subject. In one embodiment, the therapeutically effective dose is the maximum tolerated dose (MTD) of anti-BCMA CART cells that does not lead to unresolvable CRS in a subject.

In particular embodiments, compositions are preferably formulated for parenteral administration, e.g., intravascular (intravenous or intraarterial), administration. In a preferred embodiment, the compositions contemplated herein are intravenously infused into the subject in a single dose.

In one embodiment, the amount of anti-BCMA CAR+ T cells in a composition administered to a subject is at least about $5.0 \times 10^7$ cells, at least about $15.0 \times 10^7$ cells, at least about $45.0 \times 10^7$ cells, at least about $80.0 \times 10^7$ cells, or at least about $12.0 \times 10^8$ cells.

In one embodiment, the amount of anti-BCMA CAR+ T cells in a composition administered to a subject is greater than about $5.0 \times 10^7$ cells, greater than about $15.0 \times 10^7$ cells, greater than about $45.0 \times 10^7$ cells, greater than about $80.0 \times 10^7$ cells, or greater than about $12.0 \times 10^8$ cells.

In one embodiment, the amount of anti-BCMA CAR+ T cells in a composition administered to a subject is between about $5.0 \times 10^7$ cells to about $15.0 \times 10^7$ cells, between about $5.0 \times 10^7$ cells to about $45.0 \times 10^7$ cells, between about $5.0 \times 10^7$ cells to about $80.0 \times 10^7$ cells, or between about $5.0 \times 10^7$ cells to about $12.0 \times 10^8$ cells.

In one embodiment, the amount of anti-BCMA CAR+ T cells in a composition administered to a subject is between about $15.0 \times 10^7$ cells to about $45.0 \times 10^7$ cells, between about $15.0 \times 10^7$ cells to about $80.0 \times 10^7$ cells, or between about $15.0 \times 10^7$ cells to about $12.0 \times 10^8$ cells.

In one embodiment, the amount of anti-BCMA CAR+ T cells in a composition administered to a subject is at least $5.0 \times 10^7$ cells $\pm 20\%$, at least $15.0 \times 10^7$ cells $\pm 20\%$, at least $45.0 \times 10^7$ cells $\pm 20\%$, at least $80.0 \times 10^7$ cells, $\pm 20\%$ or at least $12.0 \times 10^8$ cells $\pm 20\%$.

In one embodiment, the amount of anti-BCMA CAR+ T cells in a composition administered to a subject is greater than $5.0 \times 10^7$ cells $\pm 20\%$, at least $15.0 \times 10^7$ cells $\pm 20\%$, at least $45.0 \times 10^7$ cells $\pm 20\%$, at least $80.0 \times 10^7$ cells $\pm 20\%$, or at least $12.0 \times 10^8$ cells $\pm 20\%$.

In one embodiment, the amount of anti-BCMA CAR+ T cells in a composition administered to a subject is between $5.0 \times 10^7$ cells $\pm 20\%$ to $15.0 \times 10^7$ cells $\pm 20\%$, between $5.0 \times 10^7$ cells $\pm 20\%$ to $45.0 \times 10^7$ cells $\pm 20\%$, between $5.0 \times 10^7$ cells $\pm 20\%$ to $80.0 \times 10^7$ cells $\pm 20\%$, or between $5.0 \times 10^7$ cells $\pm 20\%$ to $12.0 \times 10^8$ cells $\pm 20\%$.

In one embodiment, the amount of anti-BCMA CAR+ T cells in a composition administered to a subject is between $15.0 \times 10^7$ cells $\pm 20\%$ to $45.0 \times 10^7$ cells $\pm 20\%$, between $15.0 \times 10^7$ cells $\pm 20\%$ to $80.0 \times 10^7$ cells $\pm 20\%$, or between $15.0 \times 10^7$ cells $\pm 20\%$ to $12.0 \times 10^8$ cells $\pm 20\%$.

For uses provided herein, the cells are generally in a volume of a liter or less, can be 500 mLs or less, even 250 mLs or 100 mLs or less.

In particular embodiments, pharmaceutical compositions comprise a therapeutically effective amount of anti-BCMA CAR T cells, in combination with one or more pharmaceutically or physiologically acceptable carriers, diluents or excipients.

Pharmaceutical compositions comprising a therapeutically effective dose of anti-BCMA CAR T cells may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

The liquid pharmaceutical compositions, whether they be solutions, suspensions or other like form, may include one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In one embodiment, anti-BCMA CAR T cell compositions contemplated herein are formulated in a pharmaceutically acceptable cell culture medium. Such compositions are suitable for administration to human subjects. In particular embodiments, the pharmaceutically acceptable cell culture medium is a serum free medium.

Serum-free medium has several advantages over serum containing medium, including a simplified and better defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

Illustrative examples of serum-free media used in particular compositions includes, but is not limited to QBSF-60 (Quality Biological, Inc.), StemPro-34 (Life Technologies), and X-VIVO 10.

In one preferred embodiment, compositions comprising anti-BCMA CAR T cells contemplated herein are formulated in a solution comprising PlasmaLyte A.

In another preferred embodiment, compositions comprising anti-BCMA CAR T cells contemplated herein are formulated in a solution comprising a cryopreservation medium. For example, cryopreservation media with cryopreservation agents may be used to maintain a high cell viability outcome post-thaw. Illustrative examples of cryopreservation media used in particular compositions includes, but is not limited to, CryoStor CS10, CryoStor CS5, and CryoStor CS2.

In a more preferred embodiment, compositions comprising anti-BCMA CAR T cells contemplated herein are formulated in a solution comprising 50:50 PlasmaLyte A to CryoStor CS10.

F. Therapeutic Methods

Methods for treating multiple myeloma contemplated herein comprise administering a composition comprising a therapeutically effective amount of T cells that express an anti-BCMA CAR to a subject.

As used herein, the terms "individual" and "subject" are often used interchangeably and refer to a human that has multiple myeloma. In preferred embodiments, a subject refers to a human that has relapsed/refractory multiple myeloma.

As used herein, the term "patient" refers to a subject that has been diagnosed with multiple myeloma and more preferably, relapsed/refractory multiple myeloma.

As used herein "treatment" or "treating," includes any beneficial or desirable effect on the symptoms or pathology of multiple myeloma and more preferably, relapsed/refractory multiple myeloma, and may include even minimal reductions in one or more measurable markers of multiple myeloma and more preferably, relapsed/refractory multiple myeloma. Treatment can involve optionally either the reduction or amelioration of symptoms of a multiple myeloma, or the delaying of the progression of a multiple myeloma. "Treatment" does not necessarily indicate complete eradication or cure of a multiple myeloma, or associated symptoms thereof.

As used herein, "prevent," and similar words such as "prevented," "preventing" etc., indicate an approach for preventing, inhibiting, or reducing the likelihood of relapse of a multiple myeloma.

Multiple myeloma is a B cell malignancy of mature plasma cell morphology characterized by the neoplastic transformation of a single clone of these types of cells. These plasma cells proliferate in BM and may invade adjacent bone and sometimes the blood. Variant forms of multiple myeloma include overt multiple myeloma, smoldering multiple myeloma, plasma cell leukemia, non-secretory myeloma, IgD myeloma, osteosclerotic myeloma, solitary plasmacytoma of bone, and extramedullary plasmacytoma (see, for example, Braunwald, et al. (eds), *Harrison's Principles of Internal Medicine*, 15th Edition (McGraw-Hill 2001)).

In particular embodiments, compositions comprising a therapeutically effective amount of anti-BCMA CAR T cells are administered to a subject to treat relapsed/refractory multiple myeloma. "Relapse" refers to the diagnosis of return, or signs and symptoms of return, of a cancer after a period of improvement or remission. "Refractory" refers to a cancer that is resistant to, or non-responsive to, therapy with a particular therapeutic agent. A cancer can be refractory from the onset of treatment (i.e., non-responsive to initial exposure to the therapeutic agent), or as a result of developing resistance to the therapeutic agent, either over the course of a first treatment period or during a subsequent treatment period.

In particular embodiments, compositions contemplated herein are administered to a subject with relapsed/refractory multiple myeloma that has been unsuccessfully treated with one, two, three or more treatments, including at least one proteasome inhibitor and/or an immunomodulatory drug (IMiD). In one embodiment, the subject's multiple myeloma is refractory to three treatment regimens, including at least one proteasome inhibitor and an IMiD. In one embodiment, the subject's multiple myeloma is double-refractory to one or more treatment regimens.

Illustrative examples of proteasome inhibitors to which subject's multiple myeloma is refractory include, but are not limited to, bortezomib, and carfilzomib.

Illustrative examples of IMiDs to which subject's multiple myeloma is refractory include, but are not limited to thalidomide, lenalidomide, and pomalidomide.

Illustrative examples of other treatments, to which multiple myeloma may be refractory include, but are not limited to, dexamethasone, and antibody-based therapies selected from the group consisting of elotuzumab, daratumumab, MOR03087, isatuximab, bevacizumab, cetuximab, siltuximab, tocilizumab, elsilimomab, azintrel, rituximab, tositumomab, milatuzumab, lucatumumab, dacetuzumab, figitumumab, dalotuzumab, AVE1642, tabalumab, pembrolizumab, pidilizumab, and nivolumab.

In one embodiment, the subject's multiple myeloma is refractory to treatment with daratumumab.

In particular embodiments, the subject's multiple myeloma is refractory to treatment with an IMiD, a proteasome inhibitor, and dexamethasone.

Methods contemplated herein, may further comprise treating a subject with relapsed/refractory multiple myeloma with an autologous hematopoietic stem cell transplant, prior to the administration of the anti-BCMA CAR T cell composition.

Methods contemplated herein, may further comprise lymphodepleting the subject prior to administration of an anti-BCMA CAR T cell composition contemplated herein, e.g., for example, the lymphodepleting chemotherapy ends 1-4 days (e.g., 1, 2, 3, or 4 days) prior to the administration. In particular embodiments, the lymphodepletion comprises administering one or more of melphalan, cytoxan, cyclo phosphamide, and fludarabine. In one embodiment the subject is lymphodepleted with cyclophosphamide 300 mg/m² and fludarabine 30 mg/m² prior to administration of an anti-BCMA CAR T cell composition contemplated herein.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Construction of BCMA CARs

CARs containing murine anti-BCMA scFv antibodies were designed to contain an MND promoter operably linked to anti-BMCA scFv, a hinge and transmembrane domain from CD8a and a CD137 co-stimulatory domains followed by the intracellular signaling domain of the CD3 chain. See, e.g., FIG. 1. The anti-BMCA CAR shown in FIG. 1 comprises a CD8a signal peptide (SP) sequence for the surface expression on T cells. The polynucleotide sequence of an exemplary anti-BMCA CAR is set forth in SEQ ID NO: 10; an exemplary polypeptide sequences of a anti-BMCA CAR is set forth in SEQ ID NO: 9; and a vector map of an exemplary CAR construct is shown in FIG. 1. Table 3 shows the Identity, Genbank Reference, Source Name and Citation for the various nucleotide segments of an anti-BMCA CAR lentiviral vector.

TABLE 3

| Nucleotides | Identity | GenBank Reference | Source Name | Citation |
| --- | --- | --- | --- | --- |
| 1-185 | pUC19 plasmid backbone | Accession #L09137.2 nt 1-185 | pUC19 | New England Biolabs |
| 185-222 | Linker | Not applicable | Synthetic | Not applicable |
| 223-800 | CMV | Not Applicable | pHCMV | (1994) PNAS 91: 9564-68 |
| 801-1136 | R, U5, PBS, and packaging sequences | Accession #M19921.2 nt 454-789 | pNL4-3 | Maldarelli, et. al. (1991) J Virol: 65(11): 5732-43 |
| 1137-1139 | Gag start codon (ATG) changed to stop codon (TAG) | Not Applicable | Synthetic | Not applicable |
| 1140-1240 | HIV-1 gag sequence | Accession #M19921.2 nt 793-893 | pNL4-3 | Maldarelli, et. al. (1991) J Virol: 65(11): 5732-43 |
| 1241-1243 | HIV-1 gag sequence changed to a second stop codon | Not Applicable | Synthetic | Not applicable |
| 1244-1595 | HIV-1 gag sequence | Accession #M19921.2 nt 897-1248 | pNL4-3 | Maldarelli, et. al. (1991) J Virol: 65(11): 5732-43 |
| 1596-1992 | HIV-1 pol cPPT/CTS | Accession #M19921.2 nt 4745-5125 | pNL4-3 | Maldarelli, et. al. (1991) J Virol: 65(11): 5732-43 |
| 1993-2517 | HIV-1, isolate HXB3 env region (RRE) | Accession #M14100.1 nt 1875-2399 | PgTAT-CMV | Malim, M. H. Nature (1988) 335: 181-183 |
| 2518-2693 | HIV-1 env sequences S/A | Accession #M19921.2 nt 8290-8470 | pNL4-3 | Maldarelli, et. al. (1991) J Virol: 65(11): 5732-43 |
| 2694-2708 | Linker | Not applicable | Synthetic | Not applicable |
| 2709-3096 | MND | Not applicable | pccl-c-MNDU3c-x2 | Challita et al. (1995) J. Virol. 69: 748-755 |
| 3097-3124 | Linker | Not applicable | Synthetic | Not applicable |
| 3125-3187 | Signal peptide | Accession # NM_001768 | CD8a signal peptide | Not applicable |
| 3188-3934 | BCMA02 scFv (V$_L$1-linker-V$_H$0) | Not applicable | Synthetic | Not applicable |
| 3935-4141 | CD8a hinge and TM | Accession # NM_001768 | CD8a hinge and TM | Milone et al (2009) Mol Ther 17(8): 1453-64 |
| 4144-4269 | CD137 (4-1BB) signaling domain | Accession # NM_001561 | CD137 signaling domain | Milone et al (2009) Mol Ther 17(8): 1453-64 |

TABLE 3-continued

| Nucleotides | Identity | GenBank Reference | Source Name | Citation |
|---|---|---|---|---|
| 4270-4606 | CD3-ζ signaling domain | Accession # NM_000734 | CD3-ζ signaling domain | Milone et al (2009) Mol Ther 17(8): 1453-64 |
| 4607-4717 | HIV-1 ppt and part of 3' U3 | Accession #M19921.2 nt 9005-9110 | pNL4-3 | Maldarelli, et. al. (1991) J Virol: 65(11): 5732-43 |
| 4718-4834 | HIV-1 part of U3 (399 bp deletion) and R | Accession #M19921.2 nt 9511-9627 | pNL4-3 | Maldarelli, et. al. (1991) J Virol: 65(11): 5732-43 |
| 4835-4858 | Synthetic polyA | Not applicable | Synthetic | Levitt, N. Genes & Dev (1989) 3: 1019-1025 |
| 4859-4877 | Linker | Not applicable | Synthetic | Not Applicable |
| 4878-7350 | pUC19 backbone | Accession #L09137.2 nt 2636-2686 | pUC19 | New England Biolabs |

Example 2

Anti-BCMA CAR T Cell Manufacturing Process

Figure 2A:
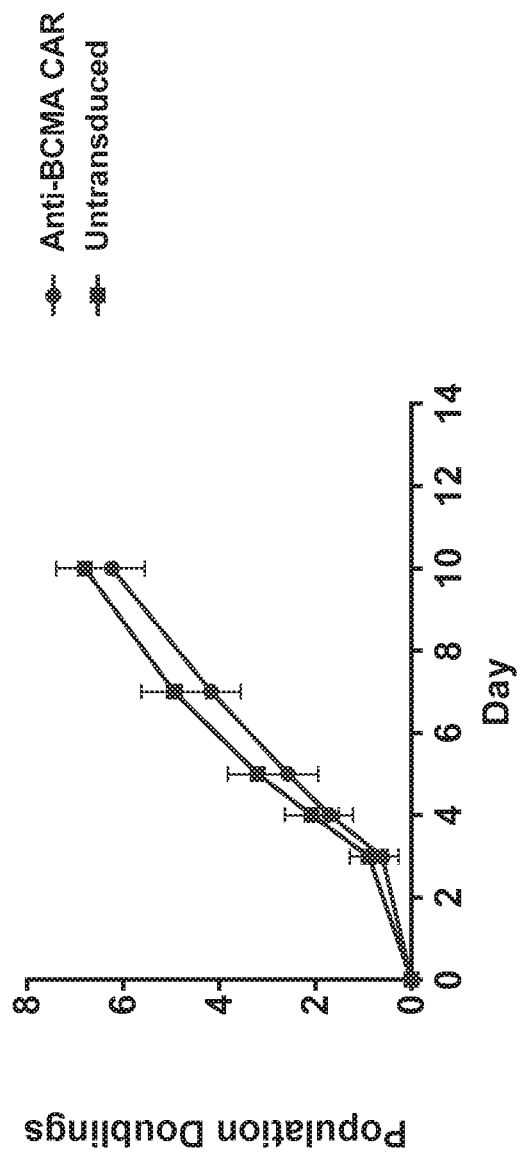
FIG. 2A shows comparable levels of expansion for anti-BCMA CAR T cells manufactured from PBMCs of 11 individual donors compared to a matched culture of untransduced donor T cells.

Unique anti-BCMA02 CAR T cell products are manufactured for each patient treatment. The reliability of the manufacturing process for anti-BCMA02 CAR T cell products was evaluated by generating anti-BCMA02 CAR T cells from 11 individual normal donor PBMC. Anti-BCMA02 CAR T cell expansion from each donor was comparable to a matched untransduced culture performed in parallel (FIG. 2A).

Figure 2B:
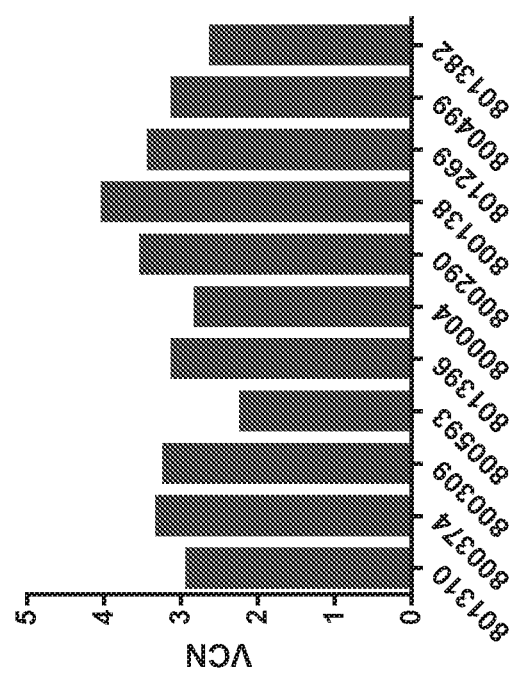
FIG. 2B shows comparable levels of lentiviral transduction efficiency (VCN) in anti-BCMA CAR T cells manufactured from PBMCs of 11 individual donors.
Figure 2C:
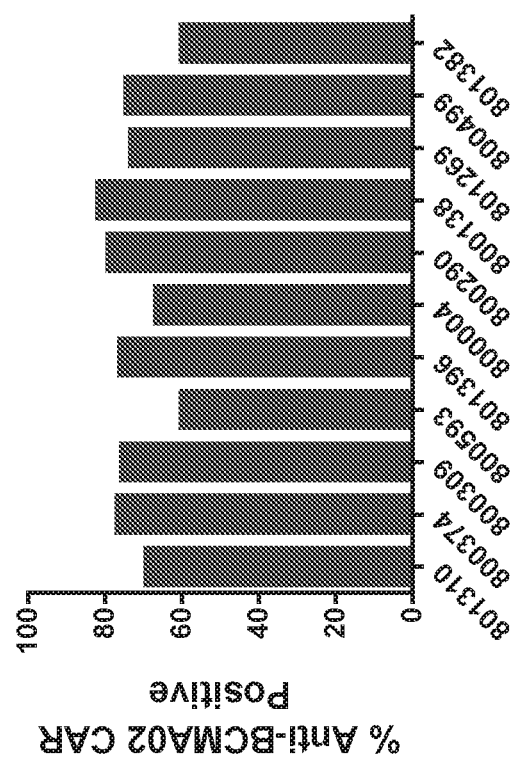
FIG. 2C shows comparable anti-BCMA CAR expression by flow cytometry in anti-BCMA CAR T cells manufactured from PBMCs of 11 individual donors.

At the end of the culture period (day 10), T cell transduction efficiency was assessed by quantitating the number of integrated lentiviruses with qPCR and lentiviral-specific primer sets (vector copy number, VCN). Anti-BCMA02 CAR T cell cultures from the 11 donors showed comparable lentiviral transduction efficiency (FIG. 2B). The frequency of anti-BCMA02 CAR positive T cells was measured by flow cytometry and BCMA expression was found to be comparable across all donors (FIG. 2C).

Figure 2D:
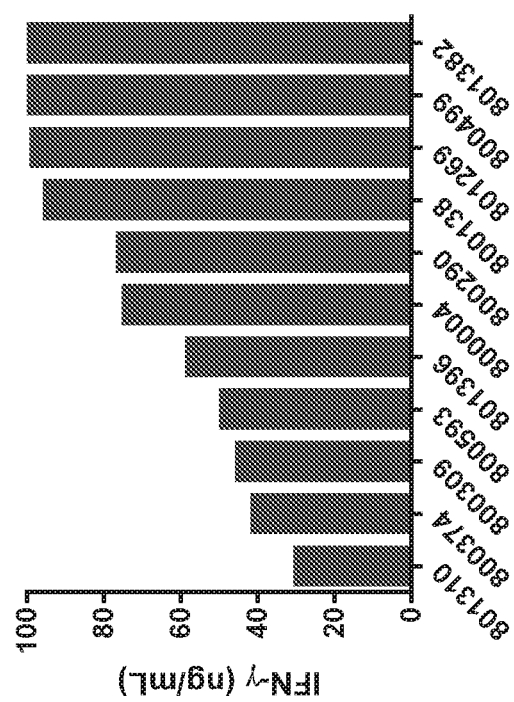
FIG. 2D shows comparable levels of IFNγ release when anti-BCMA CAR T cells manufactured from PBMCs of 11 individual donors were exposed to BCMA-expressing K562 cells.

The activity of each anti-BCMA02 CAR T cell product was assessed by IFNγ-release after co-culture with K562 cells engineered to express BCMA. All anti-BCMA CAR02 T cell products exhibited therapeutically relevant levels of IFNγ release when exposed to BCMA-expressing K562 cells (FIG. 2D).

Example 3

Anti-BCMA02 CAR T Cells Show Therapeutic Activity in Human Clinical Trials of Relapsed/Refractory Multiple Myeloma Introduction Chimeric antigen receptor (CAR) T cell therapies have demonstrated robust and sustained clinical responses observed in several hematologic malignancies. However, outside of CD19, clinical data supporting the promise of CAR T cells has been limited. The potential for CAR T cell safety and efficacy was tested in relapsed/refractory multiple myeloma (MM), a patient population with limited treatment options. To redirect T cells to MM we have targeted B cell maturation antigen (BCMA), a member of the tumor necrosis factor superfamily that is near uniformly expressed only by malignant myeloma cells, plasma cells, and some mature B cells. Initial proof of anti-BCMA activity has recently been demonstrated using T cells transduced with a gamma-retroviral vector encoding an anti-BCMA CAR with a CD28 costimulatory domain, but significant cytokine release syndrome occurred in patients with high disease burden (Ali et al., Blood 2016). Because the therapeutically effective dose of the anti-BCMA02 CAR T cells in humans is unpredictable, a dose-escalation trial was conducted.

Methods

Anti-BCMA02 CAR T cells were administered to patients with relapsed and/or refractory BCMA-positive MM who received at least 3 prior regimens, including a proteasome inhibitor and an immunomodulatory agent or who were double-refractory. Briefly, peripheral blood mononuclear cells were collected via leukapheresis and transferred to a centralized manufacturing facility for transduction and expansion. Patients were lymphodepleted with cyclophosphamide 300 mg/m$^2$ and fludarabine 30 mg/m$^2$ on study Days −5, −4 and −3 and then received a single infusion of anti-BCMA02 CAR T cells on Day 0.

The average vector copy number (VCN) for the CAR T cells was determined for the nine patients. Table 4.

TABLE 4

CAR T cell VCN

| Patient | VCN |
|---|---|
| 1 | 2.08 |
| 2 | 1.97 |
| 3 | 2.11 |
| 4 | 5.98 |
| 5 | 3.01 |
| 6 | 4.13 |
| 7 | 3.38 |
| 8 | 4.01 |
| 9 | ND |

ND = not yet determined

Results

Nine patients were infused with anti-BCMA02 CAR T cells in three dose cohorts of 5.0×10$^7$ CAR+ T cells, 15.0× 10$^7$ CAR+ T cells, and 45.0×10$^7$ CAR+ T cells. Cells were collected and successfully manufactured and released in all patients. Median age at enrollment for the 9 infused subjects was 58 years (43-68) and 67% were male. The median time from diagnosis was 6 years (1.3-8.6). The median number of prior lines of therapy was 6 (4-10), 100% of patients received at least 1 prior autologous stem cell transplant, 67% received prior daratumumab or CD38 mab, 89% received prior lenalidomide, 78% received prior pomalidomide, 100% received prior bortezomib, and 78% prior carfilzomib.

To date no dose limiting toxicities, neurotoxicities >Grade 2, or Grade 3 or higher cytokine release syndrome (CRS) have been observed. Moreover, no patients have required treatment with vasopressors, tocililuzmab or corticosteroids. Grade 1 or 2 CRS was reported in % (67%) treated patients. In addition to CRS, the most common treatment emergent adverse events were neutropenia (89%), leukopenia (67%) and anemia (44%).

Clinical responses were observed in every dose cohort. After the initial cohort, all patients remained on study and the overall response rate in the 6 patients treated at $15.0 \times 10^7$ CAR+ T cells or higher was 83%, including 2 stringent complete responses (CRs) (see Table 5). Surprisingly, at dose levels above $5.0 \times 10^7$ CAR+ T cells, all patients with bone marrow involvement at baseline have had no bone marrow disease detected at any point after day 14.

TABLE 5

Response by Dose Level & Duration

| Dose | Patient | Response | Time since bb2121 infusion (weeks) |
|---|---|---|---|
| $5.0 \times 10^7$ | 1 | PR | 13 |
| | 2* | SD | 9 |
| | 3* | PD | 8 |
| $15.0 \times 10^7$ | 4 | sCR | 28+ |
| | 5 | sCR | 21+ |
| | 6* | VGPR | 19+ |
| $45.0 \times 10^7$ | 7 | PR | 13+ |
| | 8 | SD | 11+ |
| | 9* | PR | 4+ |

*indicates patient had ≥50% bone marrow involvement at baseline.
Responses graded using IMWG Uniform Response Criteria for Multiple Myeloma.
PR: partial response, SD: stable disease, PD: progressive disease, sCR: stringent complete response, VGPR: very good partial response, NE: not yet evaluated.
+denotes ongoing response.

CAR+ T cell expansion was consistently demonstrated, and is similar to other published CART cell trials. In the 5 patients treated with >$5.0 \times 10^7$ CAR+ T cells for whom data was available, the range of peak CAR+ T cells by flow cytometry was 10 to 686 CAR+ cells/μL in peripheral blood and 4 to 527 CAR+ cells/μL in bone marrow, and the range of peak copies/μg genomic DNA in peripheral blood was 34,231 to 860,204 by PCR.

Conclusions

Anti-BCMA02 CAR T cells showed remarkable efficacy at dose levels above $5.0 \times 10^7$ CAR+ T cells, including 2 CRs and ongoing clinical response at 6 months. In contrast to results with other CAR T cell therapies, the efficacy of the anti-BCMA02 CAR T cells was accompanied by unexpectedly mild and manageable CRS, including in patients with >50% bone marrow involvement. These data support the therapeutic efficacy of anti-BCMA02 CAR T cells for relapsed/refractory multiple myeloma.

Additional dose cohorts are planned with dose levels of $80.0 \times 10^7$ and $12.0 \times 10^8$ CAR+ T cells.

Example 4

Anti-BCMA02 CAR T Cells Continue to Show Therapeutic Activity in Human Clinical Trials of Relapsed/Refractory Multiple Myeloma Twenty one patients have been infused with anti-BCMA02 CAR T cells in three dose cohorts of $5.0 \times 10^7$ CAR+ T cells (3 patients), $15.0 \times 10^7$ CAR+ T cells (6 patients), $45.0 \times 10^7$ CAR+ T cells (9 patients), and $80.0 \times 10^7$ CAR+ T cells (3 patients). Cells were collected and successfully manufactured and released in all patients. Median age at enrollment for the 9 infused subjects was 58 years (37-74) and 62% were male. The median time from diagnosis was 5 years (1.0-16.0). The median number of prior lines of therapy was 7 (3-14), 100% of patients received at least 1 prior autologous stem cell transplant, 100% previously treated with lenalidomide and bortezomib, 91% previously treated with pomalidomide and carfilzomib, 71% previously treated with daratumumab, and 29% of patients were penta-refractory (bortezomib, lenalidomide, carfilzomib, pomalidomide, daratumumab).

Figure 3:
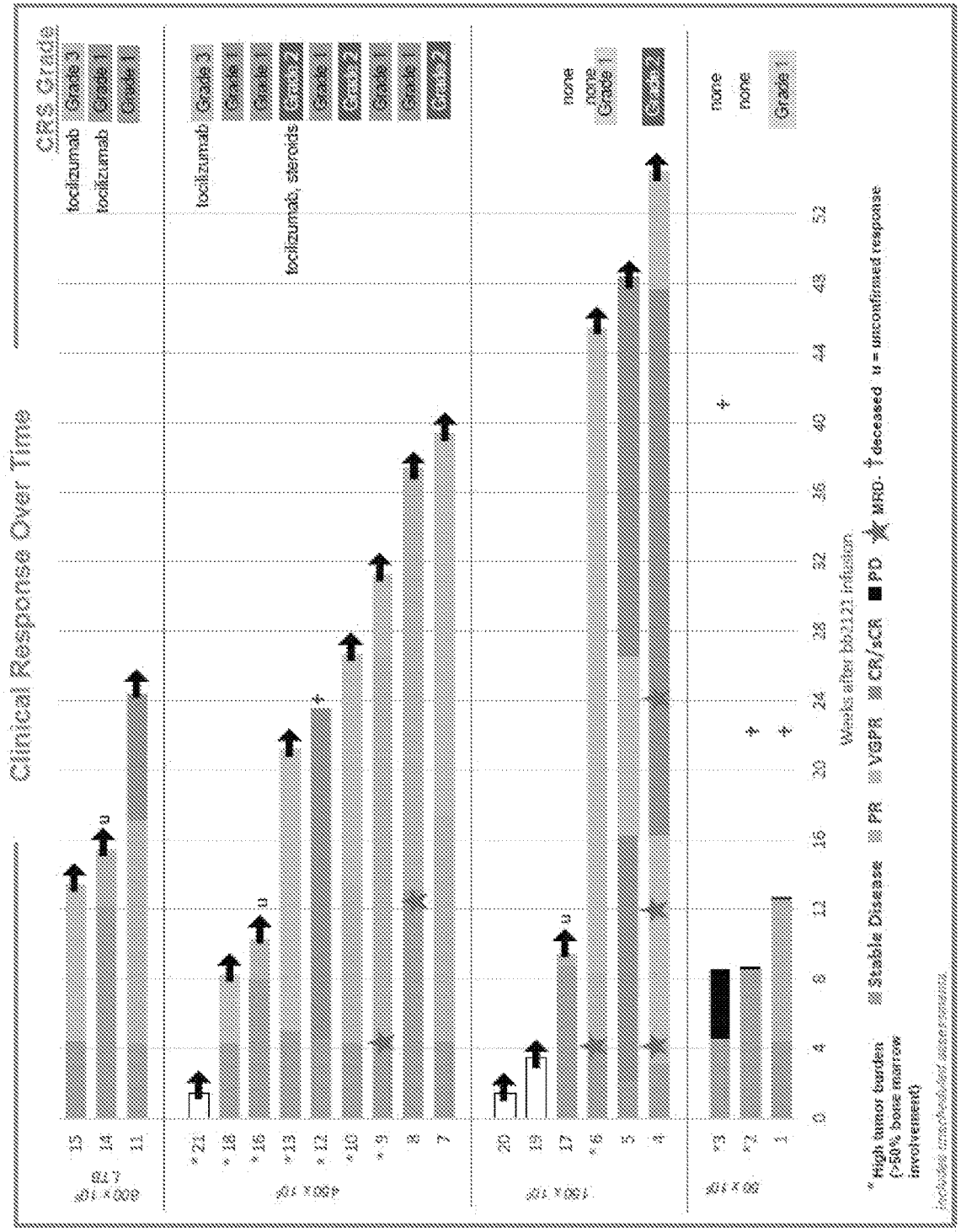
FIG. 3 shows clinical response over time of relapsed refractory multiple myeloma patients treated with anti-BCMA CAR T cells.

All patients in active dose cohorts achieved an objective response, duration up to 54 weeks. FIG. 3. CAR T cell dose, number of evaluable patients, overall response rate, best response, median lines of prior therapy, and safety for each cohort are presented in Table 6.

TABLE 6

Cohort Data

| Cohort | 1 | 2 | 3 | 4 |
|---|---|---|---|---|
| CAR+ T Cell Dose | $50 \times 10^6$ | $150 \times 10^6$ | $450 \times 10^6$ | $800 \times 10^6$ |
| Number of Patients Evaluable for Efficacy | 3 | 4 | 8 | 3 |
| Overall Response Rate in Cohort | 33% | 100% | 100% | 100% |
| Best Response | PD (1 patient) SD (1 patient) PR (1 patient) | CR (2 patients, 1 patient MRD negative) VGPR (1 patient MRD negative) PR (1 patient) | CR (1 patient*) VGPR (5 patients; 1 patient MRD negative) PR (2 patients; 1 patient MRD negative) *Patient died of unrelated cardio pulmonary arrest | VGPR (1 patient) PR (1 patient) CR (1 patient) |
| Bone Marrow Involvement | | All patients in cohorts 2, 3 and 4 with bone marrow involvement at baseline had no detectable multiple | | |

TABLE 6-continued

| | Cohort Data | | | |
|---|---|---|---|---|
| Cohort | 1 | 2 | 3 | 4 |
| | myeloma cells in their bone marrow on Day 14 or beyond. Of four patients evaluable for MRD status, all four were found to be MRD-negative. | | | |
| Median Prior Lines of Therapy | 7 (range: 3-14); all patients had at least one prior autologous stem cell transplant, as well as prior exposure to a proteasome inhibitor and an immunomodulatory agent; 71% of patients had previously received daratumumab or CD38 antibody | | | |
| Safety | 15/21 (71%) of patients had CRS, mostly Grade 1 & 2; 2 patients with Grade 3 CRS that resolved within 24 hours. 4 patients received tocilizumab, 1 (Grade 2 CRS) received steroids. The most common treatment-emergent Grade 3-4 AEs in 21 infused patients include cytopenias commonly associated with cy/flu lymphodepletion, as well as Grade 3 events of hyponatraemia (n = 4), cytokine release syndrome (n = 2), upper respiratory infection (n = 2), and syncope (n = 2). | | | |

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of treating relapsed or refractory multiple myeloma (RRMM) in a human subject who has received at least 2 prior treatment regimens including a proteosome inhibitor and an immunomodulatory agent, comprising administering intravenously to the subject a single dose of a pharmaceutical composition comprising a pharmaceutically acceptable carrier and anti-human B cell maturation antigen (BCMA) chimeric antigen receptor (CAR) human T cells, wherein the dose is greater than $45.0 \times 10^7$ and less than $80.0 \times 10^7$ anti-BCMA CAR T cells, wherein the anti-BCMA CAR comprises amino acids 22-493 of the amino acid sequence of SEQ ID NO: 9, and wherein the dose is independent of bone marrow disease in the subject.

2. The method of claim 1, wherein the subject has received at least 3 prior treatment regimens.

3. The method of claim 1, wherein the subject was treated with daratumumab, lenalidomide, pomalidomide, bortezomib, and/or carfilzomib, prior to administration of the pharmaceutical composition.

4. The method of claim 1, wherein the subject received an autologous hematopoietic stem cell transplant, prior to administration of the pharmaceutical composition.

5. The method of claim 1, wherein the subject was lymphodepleted with cyclophosphamide 300 mg/m$^2$ and fludarabine 30 mg/m$^2$ prior to administration of the pharmaceutical composition.

6. The method of claim 1 wherein the dose is independent of body weight.

7. The method of claim 1, wherein the anti-BCMA CAR is encoded by the nucleotide sequence set forth in SEQ ID NO: 10.

8. The method of claim 1, wherein the anti-BCMA CAR comprises the amino acid sequence of SEQ ID NO: 9.

9. The method of claim 1, wherein the anti-BCMA CAR T cells were produced by transduction with a lentiviral vector encoding the anti-BCMA CAR.

10. The method of claim 9, wherein the lentiviral is a human immunodeficiency virus vector.

11. The method of claim 1, wherein the T cells comprise CD8+ T cells.

12. A method of treating relapsed or refractory multiple myeloma (RRMM) in a human subject who has received at least 2 prior treatment regimens including a proteosome inhibitor and an immunomodulatory agent, comprising administering intravenously to the subject a single dose of a pharmaceutical composition comprising a pharmaceutically acceptable carrier and anti-human B cell maturation antigen (BCMA) chimeric antigen receptor (CAR) human T cells, wherein the dose is $45.0 \times 10^7 \pm 20\%$ anti-human BCMA CAR T cells, wherein the anti-BCMA CAR comprises amino acids 22-493 of the amino acid sequence of SEQ ID NO: 9, and wherein the dose is independent of bone marrow disease in the subject.

13. The method of claim 12, wherein the subject has received at least 3 prior treatment regimens.

14. The method of claim 12, wherein the subject was treated with daratumumab, lenalidomide, pomalidomide, bortezomib, and/or carfilzomib, prior to administration of the pharmaceutical composition.

15. The method of claim 12, wherein the subject was lymphodepleted with cyclophosphamide 300 mg/m$^2$ and fludarabine 30 mg/m$^2$ prior to administration of the pharmaceutical composition.

16. The method of claim 12, wherein the subject received an autologous hematopoietic stem cell transplant, prior to administration of the pharmaceutical composition.

17. The method of claim 12, wherein the dose is independent of body weight.

18. The method of claim 12, wherein the anti-BCMA CAR is encoded by the nucleotide sequence set forth in SEQ ID NO: 10.

19. The method of claim 12, wherein the anti-BCMA CAR comprises the amino acid sequence of SEQ ID NO: 9.

20. The method of claim 12, wherein the anti-BCMA CAR T cells were produced by transduction with a lentiviral vector encoding the anti-BCMA CAR.

21. The method of claim 20, wherein the lentiviral is a human immunodeficiency virus vector.

22. The method of claim 12, wherein the T cells comprise CD8+ T cells.

* * * * *

UNITED STATES PATENT AND TRADEMARK OFFICE
CERTIFICATE OF CORRECTION

| | |
|---|---|
| PATENT NO. | : 12,109,234 B2 |
| APPLICATION NO. | : 16/346393 |
| DATED | : October 8, 2024 |
| INVENTOR(S) | : Quigley et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 218 days.

Signed and Sealed this
Third Day of June, 2025

Coke Morgan Stewart
*Acting Director of the United States Patent and Trademark Office*

SEQUENCE LISTING

```
<160> NUMBER OF SEQ ID NOS: 36

<210> SEQ ID NO 1
<211> LENGTH: 15
<212> TYPE: PRT
<213> ORGANISM: Mus musculus

<400> SEQUENCE: 1

Arg Ala Ser Glu Ser Val Thr Ile Leu Gly Ser His Leu Ile His
1               5                   10                  15

<210> SEQ ID NO 2
<211> LENGTH: 7
<212> TYPE: PRT
<213> ORGANISM: mus musculus

<400> SEQUENCE: 2

Leu Ala Ser Asn Val Gln Thr
1               5

<210> SEQ ID NO 3
<211> LENGTH: 9
<212> TYPE: PRT
<213> ORGANISM: mus musculus

<400> SEQUENCE: 3

Leu Gln Ser Arg Thr Ile Pro Arg Thr
1               5

<210> SEQ ID NO 4
<211> LENGTH: 5
<212> TYPE: PRT
<213> ORGANISM: Mus musculus

<400> SEQUENCE: 4

Asp Tyr Ser Ile Asn
1               5
```

<210> SEQ ID NO 5
<211> LENGTH: 17
<212> TYPE: PRT
<213> ORGANISM: Mus musculus

<400> SEQUENCE: 5

Trp Ile Asn Thr Glu Thr Arg Glu Pro Ala Tyr Ala Tyr Asp Phe Arg
1               5                   10                  15

Gly

<210> SEQ ID NO 6
<211> LENGTH: 8
<212> TYPE: PRT
<213> ORGANISM: Mus musculus

<400> SEQUENCE: 6

Asp Tyr Ser Tyr Ala Met Asp Tyr
1               5

<210> SEQ ID NO 7
<211> LENGTH: 111
<212> TYPE: PRT
<213> ORGANISM: Mus musculus

<400> SEQUENCE: 7

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys
            100                 105                 110

<210> SEQ ID NO 8
<211> LENGTH: 117
<212> TYPE: PRT
<213> ORGANISM: Mus musculus

<400> SEQUENCE: 8

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
            100                 105                 110

Val Thr Val Ser Ser
        115

<210> SEQ ID NO 9
<211> LENGTH: 493
<212> TYPE: PRT
<213> ORGANISM: Artificial Sequence
<220> FEATURE:
<223> OTHER INFORMATION: anti-BCMA02 CAR

<400> SEQUENCE: 9

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ser Leu
            20                  25                  30

Ala Met Ser Leu Gly Lys Arg Ala Thr Ile Ser Cys Arg Ala Ser Glu
        35                  40                  45

Ser Val Thr Ile Leu Gly Ser His Leu Ile His Trp Tyr Gln Gln Lys
    50                  55                  60

Pro Gly Gln Pro Pro Thr Leu Leu Ile Gln Leu Ala Ser Asn Val Gln
65                  70                  75                  80

Thr Gly Val Pro Ala Arg Phe Ser Gly Ser Gly Ser Arg Thr Asp Phe
                85                  90                  95

Thr Leu Thr Ile Asp Pro Val Glu Glu Asp Val Ala Val Tyr Tyr
            100                 105                 110

Cys Leu Gln Ser Arg Thr Ile Pro Arg Thr Phe Gly Gly Gly Thr Lys
            115                 120                 125

Leu Glu Ile Lys Gly Ser Thr Ser Gly Ser Gly Lys Pro Gly Ser Gly
        130                 135                 140

Glu Gly Ser Thr Lys Gly Gln Ile Gln Leu Val Gln Ser Gly Pro Glu
145                 150                 155                 160

Leu Lys Lys Pro Gly Glu Thr Val Lys Ile Ser Cys Lys Ala Ser Gly
                165                 170                 175

Tyr Thr Phe Thr Asp Tyr Ser Ile Asn Trp Val Lys Arg Ala Pro Gly
            180                 185                 190

Lys Gly Leu Lys Trp Met Gly Trp Ile Asn Thr Glu Thr Arg Glu Pro
        195                 200                 205

Ala Tyr Ala Tyr Asp Phe Arg Gly Arg Phe Ala Phe Ser Leu Glu Thr
    210                 215                 220

Ser Ala Ser Thr Ala Tyr Leu Gln Ile Asn Asn Leu Lys Tyr Glu Asp
225                 230                 235                 240

Thr Ala Thr Tyr Phe Cys Ala Leu Asp Tyr Ser Tyr Ala Met Asp Tyr
                245                 250                 255

Trp Gly Gln Gly Thr Ser Val Thr Val Ser Ser Ala Ala Ala Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

| | | | | | | | | | | | | |
|---|---|---|---|---|---|---|---|---|---|---|---|---|
|Leu|Tyr|Cys|Lys|Arg|Gly|Arg|Lys|Leu|Leu|Tyr|Ile|Phe|Lys|Gln|
| | | |340| | | |345| | | |350| | | |

Pro Phe Met Arg Pro Val Gln Thr Thr Gln Glu Glu Asp Gly Cys Ser
            355                 360                 365

Cys Arg Phe Pro Glu Glu Glu Gly Gly Cys Glu Leu Arg Val Lys
        370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
                420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
            450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 10
<211> LENGTH: 1485
<212> TYPE: DNA
<213> ORGANISM: Artificial Sequence
<220> FEATURE:
<223> OTHER INFORMATION: anti-BCMA02 CAR

<400> SEQUENCE: 10

```
atggcactcc ccgtcaccgc ccttctcttg cccctcgccc tgctgctgca tgctgccagg      60
cccgacattg tgctcactca gtcacctccc agcctggcca tgagcctggg aaaaagggcc     120
accatctcct gtagagccag tgagtccgtc acaatcttgg ggagccatct tattcactgg     180
tatcagcaga agcccgggca gcctccaacc cttcttattc agctcgcgtc aaacgtccag     240
acgggtgtac ctgccagatt ttctggtagc gggtcccgca ctgattttac actgaccata     300
gatccagtgg aagaagacga tgtggccgtg tattattgtc tgcagagcag aacgattcct     360
cgcacatttg gtgggggtac taagctggag attaagggaa gcacgtccgg ctcaggaaag     420
ccgggctccg gcgagggaag cacgaagggg caaattcagc tggtccagag cggacctgag     480
ctgaaaaaac ccggcgagac tgttaagatc agttgtaaag catctggcta taccttcacc     540
gactacagca taaattgggt gaaacgggcc ctggaaaagg cctcaaatg atgggttgg     600
atcaataccg aaactaggga gcctgcttat gcatatgact ccgcgggag attcgccttt     660
tcactcgaga catctgcctc tactgcttac ctccaaataa acaacctcaa gtatgaagat     720
acagccactt acttttgcgc cctcgactat agttacgcca tggactactg ggacaggga     780
acctccgtta ccgtcagttc cgcggccgca accacaacac tgctccaag cccccccaca     840
cccgctccaa ctatagccag ccaaccattg agcctcagac tgaagcttg caggcccgca     900
gcaggaggcg ccgtccatac gcgaggcctg gacttcgcgt gtgatattta tatttgggcc     960
cctttggccg gaacatgtgg ggtgttgctt ctctcccttg tgatcactct gtattgtaag    1020
cgcgggagaa agaagctcct gtacatcttc aagcagcctt ttatgcgacc tgtgcaaacc    1080
actcaggaag aagatgggtg ttcatgccgc ttccccgagg aggaagaagg agggtgtgaa    1140
ctgagggtga atttttctag aagcgccgat gctcccgcat atcagcaggg tcagaatcag    1200
```

```
ctctacaatg aattgaatct cggcaggcga gaagagtacg atgttctgga caagagacgg    1260
ggcagggatc ccgagatggg gggaaagccc cggagaaaaa atcctcagga ggggttgtac    1320
aatgagctgc agaaggacaa gatggctgaa gcctatagcg agatcggaat gaaaggcgaa    1380
agacgcagag gcaaggggca tgacggtctg taccagggtc tctctacagc caccaaggac    1440
acttatgatg cgttgcatat gcaagccttg ccaccccgct aatga                   1485
```

<210> SEQ ID NO 11
<211> LENGTH: 184
<212> TYPE: PRT
<213> ORGANISM: Homo sapiens

<400> SEQUENCE: 11

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180
```

<210> SEQ ID NO 12
<211> LENGTH: 5
<212> TYPE: PRT
<213> ORGANISM: Artificial Sequence
<220> FEATURE:
<223> OTHER INFORMATION: Flexible peptide linker

<400> SEQUENCE: 12

```
Asp Gly Gly Gly Ser
1               5
```

<210> SEQ ID NO 13
<211> LENGTH: 5
<212> TYPE: PRT
<213> ORGANISM: Artificial Sequence
<220> FEATURE:
<223> OTHER INFORMATION: Flexible peptide linker

<400> SEQUENCE: 13

Thr Gly Glu Lys Pro

```
<210> SEQ ID NO 14
<211> LENGTH: 4
<212> TYPE: PRT
<213> ORGANISM: Artificial Sequence
<220> FEATURE:
<223> OTHER INFORMATION: Flexible peptide linker

<400> SEQUENCE: 14

Gly Gly Arg Arg
1

<210> SEQ ID NO 15
<211> LENGTH: 5
<212> TYPE: PRT
<213> ORGANISM: Artificial Sequence
<220> FEATURE:
<223> OTHER INFORMATION: Flexible peptide linker

<400> SEQUENCE: 15

Gly Gly Gly Gly Ser
1               5

<210> SEQ ID NO 16
<211> LENGTH: 14
<212> TYPE: PRT
<213> ORGANISM: Artificial Sequence
<220> FEATURE:
<223> OTHER INFORMATION: Flexible peptide linker

<400> SEQUENCE: 16

Glu Gly Lys Ser Ser Gly Ser Gly Ser Glu Ser Lys Val Asp
1               5                   10

<210> SEQ ID NO 17
<211> LENGTH: 18
<212> TYPE: PRT
<213> ORGANISM: Artificial Sequence
<220> FEATURE:
<223> OTHER INFORMATION: Flexible peptide linker

<400> SEQUENCE: 17

Lys Glu Ser Gly Ser Val Ser Ser Glu Gln Leu Ala Gln Phe Arg Ser
1               5                   10                  15

Leu Asp

<210> SEQ ID NO 18
<211> LENGTH: 8
<212> TYPE: PRT
<213> ORGANISM: Artificial Sequence
<220> FEATURE:
<223> OTHER INFORMATION: Flexible peptide linker

<400> SEQUENCE: 18

Gly Gly Arg Arg Gly Gly Gly Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Flexible peptide linker

<400> SEQUENCE: 19
```

Leu Arg Gln Arg Asp Gly Glu Arg Pro
1               5

<210> SEQ ID NO 20
<211> LENGTH: 12
<212> TYPE: PRT
<213> ORGANISM: Artificial Sequence
<220> FEATURE:
<223> OTHER INFORMATION: Flexible peptide linker

<400> SEQUENCE: 20

Leu Arg Gln Lys Asp Gly Gly Gly Ser Glu Arg Pro
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Flexible peptide linker

<400> SEQUENCE: 21

Leu Arg Gln Lys Asp Gly Gly Gly Ser Gly Gly Gly Ser Glu Arg Pro
1               5                   10                  15

<210> SEQ ID NO 22
<211> LENGTH: 18
<212> TYPE: PRT
<213> ORGANISM: Artificial Sequence
<220> FEATURE:
<223> OTHER INFORMATION: Flexible peptide linker

<400> SEQUENCE: 22

Gly Ser Thr Ser Gly Ser Gly Lys Pro Gly Ser Gly Glu Gly Ser Thr
1               5                   10                  15

Lys Gly

<210> SEQ ID NO 23
<211> LENGTH: 7
<212> TYPE: PRT
<213> ORGANISM: Artificial Sequence
<220> FEATURE:
<223> OTHER INFORMATION: protease cleavage site
<220> FEATURE:
<221> NAME/KEY: MISC_FEATURE
<222> LOCATION: (2)..(3)
<223> OTHER INFORMATION: Xaa = Any amino acid
<220> FEATURE:
<221> NAME/KEY: MISC_FEATURE
<222> LOCATION: (5)..(5)
<223> OTHER INFORMATION: Xaa = Any amino acid
<220> FEATURE:
<221> NAME/KEY: MISC_FEATURE
<222> LOCATION: (7)..(7)
<223> OTHER INFORMATION: Xaa  is Gly or Ser

<400> SEQUENCE: 23

Glu Xaa Xaa Tyr Xaa Gln Xaa
1               5

<210> SEQ ID NO 24
<211> LENGTH: 7
<212> TYPE: PRT
<213> ORGANISM: Artificial Sequence
<220> FEATURE:
<223> OTHER INFORMATION: protease cleavage site

<400> SEQUENCE: 24

```
Glu Asn Leu Tyr Phe Gln Gly
1               5
```

<210> SEQ ID NO 25
<211> LENGTH: 7
<212> TYPE: PRT
<213> ORGANISM: Artificial Sequence
<220> FEATURE:
<223> OTHER INFORMATION: protease cleavage site

<400> SEQUENCE: 25

```
Glu Asn Leu Tyr Phe Gln Ser
1               5
```

<210> SEQ ID NO 26
<211> LENGTH: 19
<212> TYPE: PRT
<213> ORGANISM: Artificial Sequence
<220> FEATURE:
<223> OTHER INFORMATION: protease cleavage site

<400> SEQUENCE: 26

```
Leu Leu Asn Phe Asp Leu Leu Lys Leu Ala Gly Asp Val Glu Ser Asn
1               5                   10                  15

Pro Gly Pro
```

<210> SEQ ID NO 27
<211> LENGTH: 19
<212> TYPE: PRT
<213> ORGANISM: Artificial Sequence
<220> FEATURE:
<223> OTHER INFORMATION: protease cleavage site

<400> SEQUENCE: 27

```
Thr Leu Asn Phe Asp Leu Leu Lys Leu Ala Gly Asp Val Glu Ser Asn
1               5                   10                  15

Pro Gly Pro
```

<210> SEQ ID NO 28
<211> LENGTH: 14
<212> TYPE: PRT
<213> ORGANISM: Artificial Sequence
<220> FEATURE:
<223> OTHER INFORMATION: protease cleavage site

<400> SEQUENCE: 28

```
Leu Leu Lys Leu Ala Gly Asp Val Glu Ser Asn Pro Gly Pro
1               5                   10
```

<210> SEQ ID NO 29
<211> LENGTH: 17
<212> TYPE: PRT
<213> ORGANISM: Artificial Sequence
<220> FEATURE:
<223> OTHER INFORMATION: protease cleavage site

<400> SEQUENCE: 29

```
Asn Phe Asp Leu Leu Lys Leu Ala Gly Asp Val Glu Ser Asn Pro Gly
1               5                   10                  15

Pro
```

<210> SEQ ID NO 30
<211> LENGTH: 20
<212> TYPE: PRT
<213> ORGANISM: Artificial Sequence

```
<220> FEATURE:
<223> OTHER INFORMATION: protease cleavage site

<400> SEQUENCE: 30

Gln Leu Leu Asn Phe Asp Leu Leu Lys Leu Ala Gly Asp Val Glu Ser
1               5                   10                  15

Asn Pro Gly Pro
            20

<210> SEQ ID NO 31
<211> LENGTH: 24
<212> TYPE: PRT
<213> ORGANISM: Artificial Sequence
<220> FEATURE:
<223> OTHER INFORMATION: protease cleavage site

<400> SEQUENCE: 31

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 32
<211> LENGTH: 40
<212> TYPE: PRT
<213> ORGANISM: Artificial Sequence
<220> FEATURE:
<223> OTHER INFORMATION: protease cleavage site

<400> SEQUENCE: 32

Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr
        35                  40

<210> SEQ ID NO 33
<211> LENGTH: 18
<212> TYPE: PRT
<213> ORGANISM: Artificial Sequence
<220> FEATURE:
<223> OTHER INFORMATION: protease cleavage site

<400> SEQUENCE: 33

Leu Asn Phe Asp Leu Leu Lys Leu Ala Gly Asp Val Glu Ser Asn Pro
1               5                   10                  15

Gly Pro

<210> SEQ ID NO 34
<211> LENGTH: 40
<212> TYPE: PRT
<213> ORGANISM: Artificial Sequence
<220> FEATURE:
<223> OTHER INFORMATION: protease cleavage site

<400> SEQUENCE: 34

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40
```

<210> SEQ ID NO 35
<211> LENGTH: 33
<212> TYPE: PRT
<213> ORGANISM: Artificial Sequence
<220> FEATURE:
<223> OTHER INFORMATION: protease cleavage site

<400> SEQUENCE: 35

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 36
<211> LENGTH: 7350
<212> TYPE: DNA
<213> ORGANISM: Artificial Sequence
<220> FEATURE:
<223> OTHER INFORMATION: anti-BCMA02 CAR vector

<400> SEQUENCE: 36

| | | |
|---|---|---|
| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgggtg | 120 |
| ttggcgggtg tcggggctgg cttaactatg cggcatcaga gcagattgta ctgagagtgc | 180 |
| accatcatat gccagcctat ggtgacattg attattgact agttattaat agtaatcaat | 240 |
| tacgggtca ttagttcata gcccatatat ggagttccgc gttacataac ttacggtaaa | 300 |
| tggcccgcct ggctgaccgc ccaacgaccc cgcccattg acgtcaataa tgacgtatgt | 360 |
| tcccatagta acgccaatag ggactttcca ttgacgtcaa tgggtggagt atttacggta | 420 |
| aactgcccac ttggcagtac atcaagtgta tcatatgcca agtacgcccc ctattgacgt | 480 |
| caatgacggt aaatggcccg cctggcatta tgcccagtac atgaccttat gggactttcc | 540 |
| tacttggcag tacatctacg tattagtcat cgctattacc atggtgatgc ggttttggca | 600 |
| gtacatcaat gggcgtggat agcggtttga ctcacgggga tttccaagtc tccaccccat | 660 |
| tgacgtcaat gggagtttgt tttggcacca aaatcaacgg gactttccaa atgtcgtaa | 720 |
| caactccgcc ccattgacgc aaatgggcgg taggcgtgta cggtgggagg tctatataag | 780 |
| cagagctcgt ttagtgaacc gggtctctct ggttagacca gatctgagcc tgggagctct | 840 |
| ctggctaact agggaaccca ctgcttaagc ctcaataaag cttgccttga gtgctcaaag | 900 |
| tagtgtgtgc ccgtctgttg tgtgactctg gtaactagag atccctcaga cccttttagt | 960 |
| cagtgtggaa aatctctagc agtggcgccc gaacagggac ttgaaagcga agtaaagcc | 1020 |
| agaggagatc tctcgacgca ggactcggct tgctgaagcg cgcacggcaa gaggcgaggg | 1080 |
| gcggcgactg gtgagtacgc caaaattttt gactagcgga ggctagaagg agagagtagg | 1140 |
| gtgcgagagc gtcggtatta agcggggag aattagataa atgggaaaaa attcggttaa | 1200 |
| ggccaggggg aaagaaacaa tataaactaa aacatatagt tagggcaagc agggagctag | 1260 |
| aacgattcgc agttaatcct ggccttttag agacatcaga aggctgtaga caaatactgg | 1320 |
| gacagctaca accatcccct cagacaggat cagaagaact tagatcatta tataatacaa | 1380 |
| tagcagtcct ctattgtgtg catcaaagga tagatgtaaa agacaccaag gaagccttag | 1440 |
| ataagataga ggaagagcaa aacaaaagta agaaaaaggc acagcaagca gcagctgaca | 1500 |

-continued

```
caggaaacaa cagccaggtc agccaaaatt accctatagt gcagaacctc caggggcaaa    1560
tggtacatca ggccatatca cctagaactt taaattaaga cagcagtaca aatggcagta    1620
ttcatccaca attttaaaag aaaaggggg attgggggt acagtgcagg ggaaagaata      1680
gtagacataa tagcaacaga catacaaact aaagaattac aaaaacaaat tacaaaaatt    1740
caaaattttc gggtttatta cagggacagc agagatccag tttggaaagg accagcaaag    1800
ctcctctgga aaggtgaagg ggcagtagta atacaagata atagtgacat aaaagtagtg    1860
ccaagaagaa aagcaaagat catcagggat tatggaaaac agatggcagg tgatgattgt    1920
gtggcaagta gacaggatga ggattaacac atggaaaaga ttagtaaaac accatagctc    1980
tagagcgatc ccgatcttca gacctggagg aggagatatg agggacaatt ggagaagtga    2040
attatataaa tataaagtag taaaaattga accattagga gtagcaccca ccaaggcaaa    2100
gagaagagtg gtgcagagag aaaaaagagc agtgggaata ggagctttgt tccttgggtt    2160
cttgggagca gcaggaagca ctatgggcgc agcgtcaatg acgctgacgg tacaggccag    2220
acaattattg tctggtatag tgcagcagca gaacaatttg ctgagggcta ttgaggcgca    2280
acagcatctg ttgcaactca cagtctgggg catcaagcag ctccaggcaa gaatcctggc    2340
tgtggaaaga tacctaaagg atcaacagct cctggggatt tggggttgct ctggaaaact    2400
catttgcacc actgctgtgc cttggaatgc tagttggagt aataaatctc tggaacagat    2460
ttggaatcac acgacctgga tggagtggga cagagaaatt aacaattaca caagcttggt    2520
aggtttaaga atagtttttg ctgtactttc tatagtgaat agagttaggc agggatattc    2580
accattatcg tttcagaccc acctcccaac cccgagggga cccgacaggc ccgaaggaat    2640
agaagaagaa ggtggagaga gagacagaga cagatccatt cgattagtga acggatccat    2700
ctcgacggaa tgaagacccc acctgtaggt ttggcaagct aggatcaag gttaggaaca     2760
gagagacagc agaatatggg ccaaacagga tatctgtggt aagcagttcc tgccccggct    2820
cagggccaag aacagttgga acagcagaat atgggccaaa caggatatct gtggtaagca    2880
gttcctgccc cggctcaggg ccaagaacag atggtcccca gatgcggtcc cgccctcagc    2940
agtttctaga gaaccatcag atgtttccag ggtgccccaa ggacctgaaa tgaccctgtg    3000
ccttatttga actaaccaat cagttcgctt ctcgcttctg ttcgcgcgct tctgctcccc    3060
gagctcaata aaagagccca caaccccctca ctcggcgcga ttcacctgac gcgtctacgc    3120
caccatggca ctccccgtca ccgcccttct cttgcccctc gcctgctgc tgcatgctgc     3180
caggcccgac attgtgctca ctcagtcacc tcccagcctg gccatgagcc tgggaaaaag    3240
ggccaccatc tcctgtagag ccagtgagtc cgtcacaatc ttggggagcc atcttattca    3300
ctggtatcag cagaagcccg ggcagcctcc aaccccttctt attcagctcg cgtcaaacgt    3360
ccagacgggt gtacctgcca gattttctgg tagcgggtcc cgcactgatt ttacactgac    3420
catagatcca gtggaagaag acgatgtggc cgtgtattat tgtctgcaga gcagaacgat    3480
tcctcgcaca tttggtgggg gtactaagct ggagattaag ggaagcacgt ccggctcagg    3540
gaagccgggc tccggcgagg gaagcacgaa ggggcaaatt cagctggtcc agagcggacc    3600
tgagctgaaa aaaccggcg agactgttaa gatcagttgt aaagcatctg ctatacctt     3660
caccgactac agcataaatt gggtgaaacg ggcccctgga aagggcctca aatggatggg    3720
ttggatcaat accgaaacta gggagcctgc ttatgcatat gacttccgcg ggagattcgc    3780
cttttcactc gagacatctg cctctactgc ttacctccaa ataaacaacc tcaagtatga    3840
agatacagcc acttactttt gcgccctcga ctatagttac gccatggact actggggaca    3900
```

```
gggaacctcc gttaccgtca gttccgcggc cgcaaccaca acacctgctc caaggccccc    3960
cacacccgct ccaactatag ccagccaacc attgagcctc agacctgaag cttgcaggcc    4020
cgcagcagga ggcgccgtcc atacgcgagg cctggacttc gcgtgtgata tttatatttg    4080 ggccccttg gccggaacat gtggggtgtt gcttctctcc cttgtgatca ctctgtattg    4140
taagcgcggg agaaagaagc tcctgtacat cttcaagcag cctttatgc gacctgtgca    4200 aaccactcag gaagaagatg ggtgttcatg ccgcttcccc gaggaggaag aaggagggtg    4260
tgaactgagg gtgaaatttt ctagaagcgc cgatgctccc gcatatcagc agggtcagaa    4320
tcagctctac aatgaattga atctcggcag gcgagaagag tacgatgttc tggacaagag    4380
acggggcagg gatcccgaga tggggggaaa gccccggaga aaaatcctc aggagggtt    4440 gtacaatgag ctgcagaagg acaagatggc tgaagcctat agcgagatcg aatgaaagg    4500 cgaaagacgc agaggcaagg ggcatgacgg tctgtaccag ggtctctcta cagccaccaa    4560
ggacacttat gatgcgttgc atatgcaagc cttgccaccc cgctaatgac aggtacctt    4620 aagaccaatg acttacaagg cagctgtaga tcttagccac ttttaaaag aaaagggggg    4680 actggaaggg ctaattcact cccaaagaag acaagatctg cttttgcct gtactgggtc    4740 tctctggtta gaccagatct gagcctggga gctctctggc taactaggga acccactgct    4800
taagcctcaa taaagcttgc cttgagtgct tcaatgtgtg tgttggtttt ttgtgtgtcg    4860
aaattctagc gattctagct tggcgtaatc atggtcatag ctgtttcctg tgtgaaattg    4920
ttatccgctc acaattccac acaacatacg agccggaagc ataaagtgta aagcctgggg    4980
tgcctaatga gtgagctaac tcacattaat tgcgttgcgc tcactgcccg ctttccagtc    5040
gggaaacctg tcgtgccagc tgcattaatg aatcggccaa cgcgcgggga gaggcggttt    5100
gcgtattggg cgctcttccg cttcctcgct cactgactcg ctgcgctcgg tcgttcggct    5160
gcggcgagcg gtatcagctc actcaaaggc ggtaatacgg ttatccacag aatcagggga    5220
taacgcagga aagaacatgt gagcaaaagg ccagcaaaag gccaggaacc gtaaaaaggc    5280
cgcgttgctg gcgtttttcc ataggctccg ccccctgac gagcatcaca aaaatcgacg    5340
ctcaagtcag aggtggcgaa acccgacagg actataaaga taccaggcgt ttccccctgg    5400
aagctccctc gtgcgctctc ctgttccgac cctgccgctt accggatacc tgtccgcctt    5460
tctcccttcg ggaagcgtgg cgctttctca gctcacgc tgtaggtatc tcagttcggt    5520
gtaggtcgtt cgctccaagc tgggctgtgt gcacgaaccc cccgttcagc ccgaccgctg    5580
cgccttatcc ggtaactatc gtcttgagtc caacccggta agacacgact tatcgccact    5640
ggcagcagcc actggtaaca ggattagcag agcgaggtat gtaggcggtg ctacagagtt    5700
cttgaagtgg tggcctaact acggctacac tagaagaaca gtatttggta tctgcgctct    5760
gctgaagcca gttaccttcg gaaaaagagt tggtagctct tgatccggca aacaaaccac    5820
cgctggtagc ggtggttttt ttgtttgcaa gcagcagatt acgcgcagaa aaaaaggatc    5880
tcaagaagat cctttgatct tttctacggg gtctgacgct cagtggaacg aaaactcacg    5940
ttaagggatt ttggtcatga gattatcaaa aaggatcttc acctagatcc ttttaaatta    6000
aaaatgaagt tttaaatcaa tctaaagtat atatgagtaa acttggtctg acagttacca    6060
atgcttaatc agtgaggcac ctatctcagc gatctgtcta tttcgttcat ccatagttgc    6120
ctgactcccc gtcgtgtaga taactacgat acgggagggc ttaccatctg gccccagtgc    6180
tgcaatgata ccgcgagacc cacgctcacc ggctccagat ttatcagcaa taaaccagcc    6240
```

```
agccggaagg gccgagcgca gaagtggtcc tgcaacttta tccgcctcca tccagtctat    6300
taattgttgc cgggaagcta gagtaagtag ttcgccagtt aatagtttgc gcaacgttgt    6360
tgccattgct acaggcatcg tggtgtcacg ctcgtcgttt ggtatggctt cattcagctc    6420
cggttcccaa cgatcaaggc gagttacatg atcccccatg ttgtgcaaaa aagcggttag    6480
ctccttcggt cctccgatcg ttgtcagaag taagttggcc gcagtgttat cactcatggt    6540
tatggcagca ctgcataatt ctcttactgt catgccatcc gtaagatgct tttctgtgac    6600
tggtgagtac tcaaccaagt cattctgaga atagtgtatg cggcgaccga gttgctcttg    6660
cccggcgtca atacgggata ataccgcgcc acatagcaga actttaaaag tgctcatcat    6720
tggaaaacgt tcttcggggc gaaaactctc aaggatctta ccgctgttga gatccagttc    6780
gatgtaaccc actcgtgcac ccaactgatc ttcagcatct tttactttca ccagcgtttc    6840
tgggtgagca aaaacaggaa ggcaaaatgc cgcaaaaaag ggaataaggg cgacacggaa    6900
atgttgaata ctcatactct tcctttttca atattattga agcatttatc agggttattg    6960
tctcatgagc ggatacatat ttgaatgtat ttagaaaaat aaacaaatag gggttccgcg    7020
cacatttccc cgaaaagtgc cacctgggac tagcttttg caaaagccta ggcctccaaa    7080
aaagcctcct cactacttct ggaatagctc agaggccgag gcggcctcgg cctctgcata    7140
aataaaaaaa attagtcagc catggggcgg agaatgggcg gaactgggcg gagttagggg    7200
cgggatgggc ggagttaggg gcgggactat ggttgctgac taattgagat gagcttgcat    7260
gccgacattg attattgact agtccctaag aaaccattct tatcatgaca ttaacctata    7320
aaaataggcg tatcacgagg ccctttcgtc                                    7350
```